United States Patent
Swayze et al.

(10) Patent No.: US 10,813,703 B2
(45) Date of Patent: Oct. 27, 2020

(54) ROBOTIC SURGICAL SYSTEM WITH ENERGY APPLICATION CONTROLS

(71) Applicant: Ethicon Endo-Surgery, LLC, Guaynabo, PR (US)

(72) Inventors: Jeffrey S. Swayze, Hamilton, OH (US); Mark D. Overmyer, Cincinnati, OH (US); David C. Yates, West Chester, OH (US); Frederick E. Shelton, IV, Hillsboro, OH (US); Geoffrey S. Strobl, Williamsburg, OH (US); Jason L. Harris, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 840 days.

(21) Appl. No.: 15/237,700

(22) Filed: Aug. 16, 2016

(65) Prior Publication Data
US 2018/0049817 A1    Feb. 22, 2018

(51) Int. Cl.
*A61B 34/30* (2016.01)
*A61B 18/14* (2006.01)
(Continued)

(52) U.S. Cl.
CPC ...... *A61B 34/30* (2016.02); *A61B 17/320092* (2013.01); *A61B 18/14* (2013.01);
(Continued)

(58) Field of Classification Search
CPC ........ A61B 2090/064; A61B 2090/065; A61B 2018/00666; A61B 2018/00702;
(Continued)

(56) References Cited

U.S. PATENT DOCUMENTS

| 5,190,517 A | * | 3/1993 | Zieve | ................. A61B 18/1206 604/22 |
| 8,114,345 B2 | | 2/2012 | Dlugos, Jr. et al. | |

(Continued)

OTHER PUBLICATIONS

Correlated Solutions, "Principle of Digital Image Correlation," 2013 (http://correlatedsolutions.com/digital-image-correlation/).
(Continued)

*Primary Examiner* — Linda C Dvorak
*Assistant Examiner* — Ryan T Clark
(74) *Attorney, Agent, or Firm* — Mintz Levin Cohn Ferris Glovsky and Popeo, P.C.

(57) ABSTRACT

A robotic surgical system is provided that includes an electromechanical tool coupled to a surgical instrument such as an end effector of the tool is adapted to apply ultrasound and/or radiofrequency (RF) energy to tissue when the end effector is in contact with the tissue. The end effector is configured to measure force exerted by the tissue on the end effector, which corresponds to tension at the tissue engaged by the end effector. A controller operatively coupled to the tool and the arm is configured to adjust a power applied to the tissue based on the measured force on the end effector. The controller can also adjust a type of energy such that one or both ultrasound and RF energy is selected to be applied to the tissue, based on measured force exerted by the tissue on the end effector.

17 Claims, 19 Drawing Sheets

(51) Int. Cl.
*A61B 17/32* (2006.01)
*A61B 18/00* (2006.01)
*A61B 90/00* (2016.01)

(52) U.S. Cl.
CPC .............. *A61B 18/1445* (2013.01); *A61B 2017/320093* (2017.08); *A61B 2017/320094* (2017.08); *A61B 2017/320095* (2017.08); *A61B 2018/00672* (2013.01); *A61B 2018/00678* (2013.01); *A61B 2018/00702* (2013.01); *A61B 2018/00791* (2013.01); *A61B 2018/00994* (2013.01); *A61B 2090/064* (2016.02); *A61B 2090/065* (2016.02)

(58) Field of Classification Search
CPC .......... A61B 2018/00994; A61B 2018/00672; A61B 2018/00678
See application file for complete search history.

(56) References Cited

U.S. PATENT DOCUMENTS

| | | |
|---|---|---|
| 8,882,792 B2 | 11/2014 | Dietz et al. |
| 8,915,842 B2 | 12/2014 | Weisenburgh, II et al. |
| 8,931,682 B2 | 1/2015 | Timm et al. |
| 8,945,098 B2 | 2/2015 | Seibold et al. |
| 2008/0081948 A1 | 4/2008 | Weisenburgh et al. |
| 2011/0118709 A1 | 5/2011 | Burbank |
| 2011/0118778 A1 | 5/2011 | Burbank |
| 2013/0282052 A1 | 10/2013 | Aranyi et al. |
| 2013/0296850 A1* | 11/2013 | Olson ................ A61B 18/1492 606/41 |
| 2014/0005718 A1 | 1/2014 | Shelton, IV et al. |
| 2014/0088612 A1* | 3/2014 | Bartol ................ A61B 5/6852 606/130 |

OTHER PUBLICATIONS

U.S. Appl. No. 15/131,963 entitled "Method for Operating a Surgical Instrument" filed Apr. 18, 2016.
U.S. Appl. No. 15/177,430 entitled "Surgical Instrument With User Adaptable Techniques" filed Jun. 9, 2016.

* cited by examiner

ROBOTIC SURGICAL SYSTEM WITH ENERGY APPLICATION CONTROLS

FIELD

Methods and devices are provided for robotic surgery, and in particular for communicating with and controlling robotic tools.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

A robotic surgical system and corresponding methods are provided for cutting and cauterizing tissue.

In some aspects, a surgical system is provided that in some implementations includes an electromechanical arm configured for movement in multiple axes, an electromechanical tool, and a controller operatively coupled to the electromechanical arm and the electromechanical tool. The electromechanical tool has an instrument shaft and an end effector formed thereon, the electromechanical tool being configured to be mounted on the electromechanical arm, and the electromechanical tool being configured to move with or relative to the electromechanical arm and apply energy to tissue engaged by the end effector. The controller is configured to receive, during an application of at least one type of energy to the tissue, a plurality of measurements of a plurality of parameters of the tissue, and adjust, based on the received plurality of measurements, at least one of level and type of energy applied to the tissue by the end effector.

The surgical system can vary in any number of ways. For example, the at least one type of energy can include radio frequency (RF) energy and ultrasonic energy.

In some embodiments, the plurality of parameters include temperature at the tissue. The controller can be configured to adjust the power by increasing the power when the temperature of the tissue is below a first threshold value and decreasing the power when the temperature of the tissue is above a second threshold value.

In some embodiments, the plurality of parameters include force exerted by the tissue on the end effector. The end effector can also include a strain gauge adapted to measure the force by measuring a load on the end effector. The force exerted by the tissue on the end effector can correspond to a velocity of a movement of the end effector through and/or along the tissue.

The controller can be configured to adjust the power by decreasing the power when the force exerted by the tissue on the end effector is below a first threshold value and increasing the power when the force exerted by the tissue on the end effector is above a second threshold value. The power can remain substantially constant when the force exerted by the tissue on the end effector is equal to or above the first threshold value and is equal to or below the second threshold value.

In some embodiments, the controller can be configured to adjust the power by causing the end effector to apply an additional type of energy when the force exerted by the tissue on the end effector exceeds a threshold value.

In some embodiments, the controller is configured to adjust the type of energy by causing the end effector to switch between application of ultrasound and RF energy based on the measured force exerted by the tissue on the end effector.

The electromechanical tool can be configured to apply energy to the tissue when the tissue is held by the end effector.

In some aspects, a method of operating a surgical instrument is provided that in some implementations includes applying at least one type of energy to a tissue using a surgical instrument formed on an instrument shaft of an electromechanical tool, the electromechanical tool being configured to be mounted on the electromechanical arm, receiving, during an application of the at least one type of energy to the tissue, a plurality of measurements of at least one parameter of the tissue, and adjusting, based on the plurality of measurements, at least one of a level and type of energy applied to the tissue by the end effector.

The method can vary in any number of ways. For example, the at least one type of energy can include radio frequency (RF) energy and ultrasonic energy.

In some embodiments, the at least one parameter can include a temperature of the tissue. The adjusting of the power can include increasing the power when the temperature of the tissue is below a first threshold value and decreasing the power when the temperature of the tissue is above a second threshold value.

In some embodiments, the at least one parameter includes a tension at the tissue. The method can further comprise measuring a load on the end effector, wherein the load on the end effector corresponds to a force exerted by the tissue against the end effector, and wherein the force exerted by the tissue corresponds to the tension at the tissue. The tension at the tissue can correspond to a velocity of a movement of the end effector through the tissue. The adjusting of the power can include decreasing the power when the tension at the tissue is below a first threshold value and increasing the power when the tension at the tissue is above a second threshold value.

In some embodiments, the adjusting of the type of energy can includes causing the end effector to apply an additional type of energy when the tension at the tissue exceeds a threshold.

It is to be understood that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

BRIEF DESCRIPTION OF THE DRAWINGS

The invention will be more fully understood from the following detailed description taken in conjunction with the accompanying drawings, in which.

Figure 1:
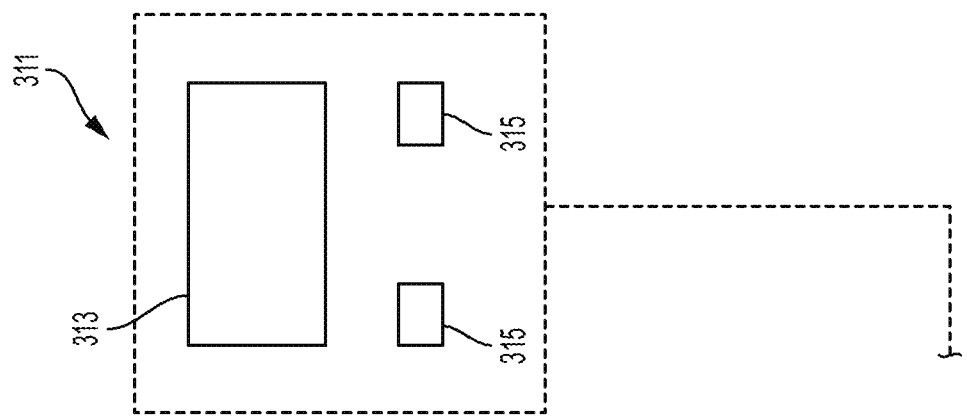
FIG. 1 illustrates a perspective view of an embodiment of a surgical robotic system.
Figure 1:
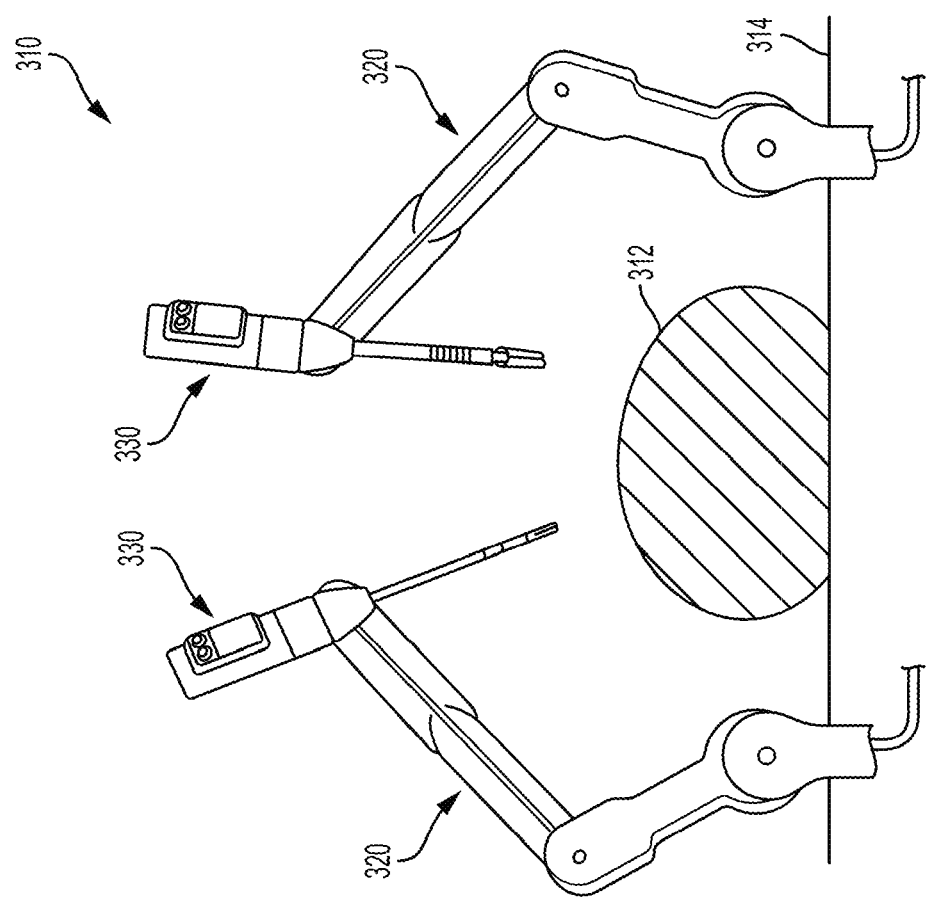

Like labels are used to refer to same or similar items in the drawings.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, one or more forms of energy can be used to treat (e.g., cut and cauterize) tissue during surgical procedures. Certain surgical instruments can be adapted to apply ultrasonic energy and/or radio frequency (RF) energy, which acts to cut the tissue while simultaneously creating a seal in the tissue by denaturing the proteins (e.g., collagen) present within the tissue. During the treatment of tissue, such surgical instruments are typically maneuvered manually (e.g., a surgeon), based on subjective parameters such as feel and/or experience.

The amount of energy (e.g., RF and/or ultrasonic) that is applied when treating tissue is critical. Particularly, a sufficient amount of energy must be applied in order to ensure that the tissue is properly cauterized and sealed. But the amount of energy that is applied can vary depending on the speed at which the surgical instrument is moved along or through the tissue. Here, subjective control over the motion of the instrument can introduce irregularities into the treatment process. For example, tissue may be subject to a "cold cut" (e.g., cut without being cauterized) when a fast moving instrument delivers only a small amount of energy along the path of the instrument. Alternately, a slow moving or lingering instrument can apply an excessive amount of energy thereby overheating and damaging the tissue.

Thus, according to implementations of a robotic surgical system described herein, the robotic system can determine an appropriate amount of energy to apply during the treatment of tissue. For instance, in some embodiments, the instrument can be configured to sense parameters including, for example, tissue temperature and tension. The tension exhibited by the tissue can indicate a velocity of the instrument's movement through tissue. The robotic system can adjust an amount of energy applied to the tissue based on the parameters sensed by the instrument. This automatic adjustment of energy based on sensed parameters can eliminate operational errors (e.g., cold cutting, overheating) that stem from a human operator's subjective control over the movement of the surgical instrument. The parameter(s) can be sensed via one or more sensors on the tool or end effector that is applying the energy to tissue, or by one or more sensors located remotely from the end effector or tool that is applying the energy, such as an adjacent end effector or surgical tool that may be mounted on an adjacent robotic arm.

Robotic Surgical Systems

The systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

Robotic System

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
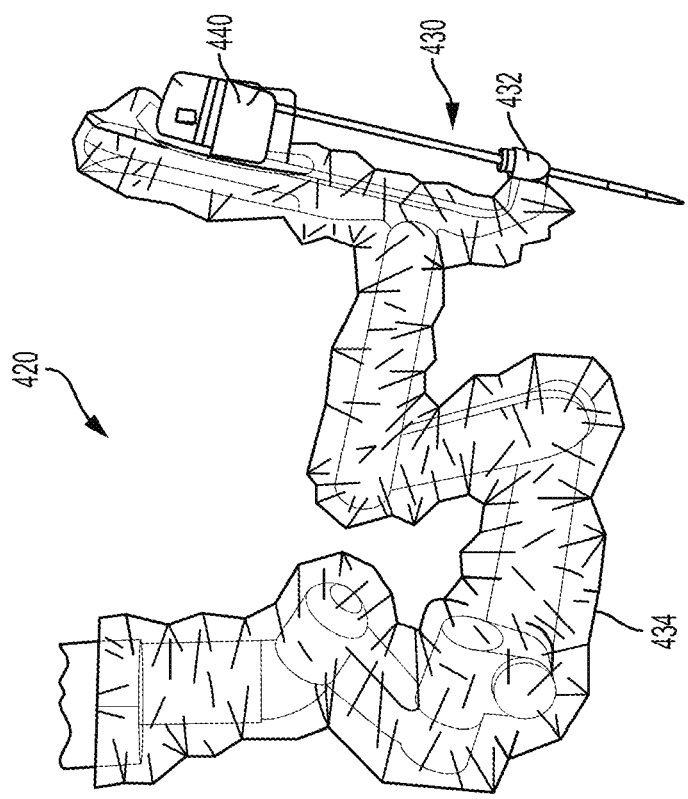
FIG. 2 illustrates an embodiment of a robotic arm and a tool assembly releasably coupled to the robotic arm.

FIG. 2 illustrates one embodiment of a robotic arm 420 and a tool assembly 430 releasably coupled to the robotic arm 420. The robotic arm 420 can support and move the associated tool assembly 430 along one or more mechanical degrees of freedom (e.g., all six Cartesian degrees of freedom, five or fewer Cartesian degrees of freedom, etc.).

The robotic arm 420 can include a tool driver 440 at a distal end of the robotic arm 420, which can assist with controlling features associated with the tool assembly 430. The robotic arm 420 can also include an entry guide 432 (e.g., a cannula mount or cannula) that can be a part of or removably coupled to the robotic arm 420, as shown in FIG. 2. A shaft 436 of the tool assembly 430 can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments (e.g., the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile surgical field.

Figure 3:
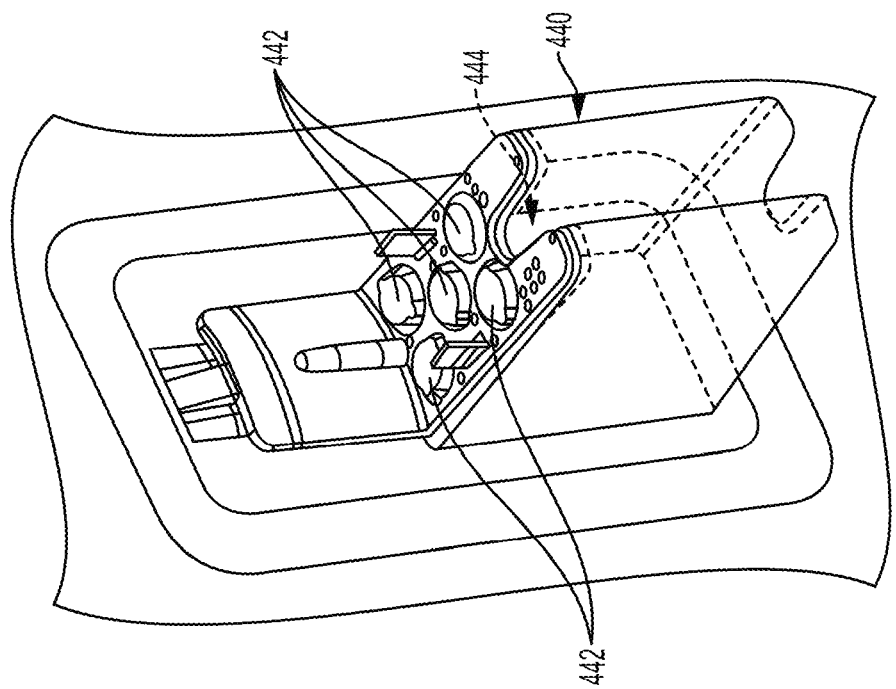
FIG. 3 illustrates an embodiment of a tool driver.

FIG. 3 illustrates the tool driver 440 in more detail. As shown, the tool driver 440 includes one or more motors, e.g., five motors 442 are shown, that control a variety of movements and actions associated with the tool assembly 430, as will be described in greater detail below. For example, each motor 442 can couple to and/or interact with an activation feature (e.g., gear) associated with the tool assembly 430 for controlling one or more actions and movements that can be performed by the tool assembly 430, such as for assisting with performing a surgical operation. The motors 442 are accessible on the upper surface of the tool driver 440, and thus the tool assembly is configured to mount on top of the tool driver 440 to couple thereto. The tool driver 440 also includes a shaft-receiving channel 444 formed in a sidewall thereof for receiving the shaft of the tool assembly 430. In other embodiments, the shaft can extend through on opening in the tool driver 440, or the two components can mate in various other configurations.

Figure 4:
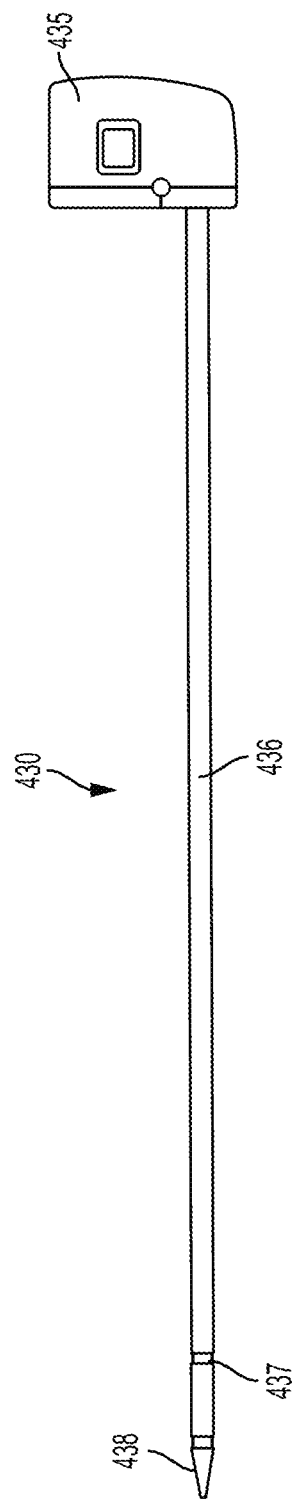
FIG. 4 illustrates an embodiment of a tool assembly uncoupled from a robotic arm.

FIG. 4 illustrates the tool assembly 430 uncoupled from the robotic arm 420. The tool assembly 430 includes a housing or puck 435 coupled to a proximal end of a shaft 436 and an end effector 438 coupled to a distal end of the shaft 436. The puck 435 can include coupling features that assist with releasably coupling the puck 435 to the tool driver 440 of the robotic arm 420. The puck 435 can include gears and/or actuators that can be actuated by the one or more motors 442 in the driver 440, as will be described in greater detail below. The gears and/or actuators in the puck 435 can control the operation of various features associated with the end effector 438 (e.g., clamping, firing, rotation, articulation, energy delivery, etc.), as well as control the movement of the shaft 436 (e.g., rotation of the shaft).

The shaft 436 can be fixed to the puck 435, or it can be releasably coupled to the puck 435 such that the shaft 436 can be interchangeable with other shafts. This can allow a single puck 435 to be adaptable to various shafts 436 having different end effectors 438. The shaft 436 can include actuators and connectors that extend along the shaft and assist with controlling the actuation and/or movement of the end effector 438 and/or shaft 436. The shaft 436 can also include one or more joints or wrists 437 that allow a part of the shaft 436 or the end effector 438 to articulate relative to the longitudinal axis of the shaft 436. This can allow for fine movements and various angulation of the end effector 438 relative to the longitudinal axis of the shaft 436. The end effector 438 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 5:
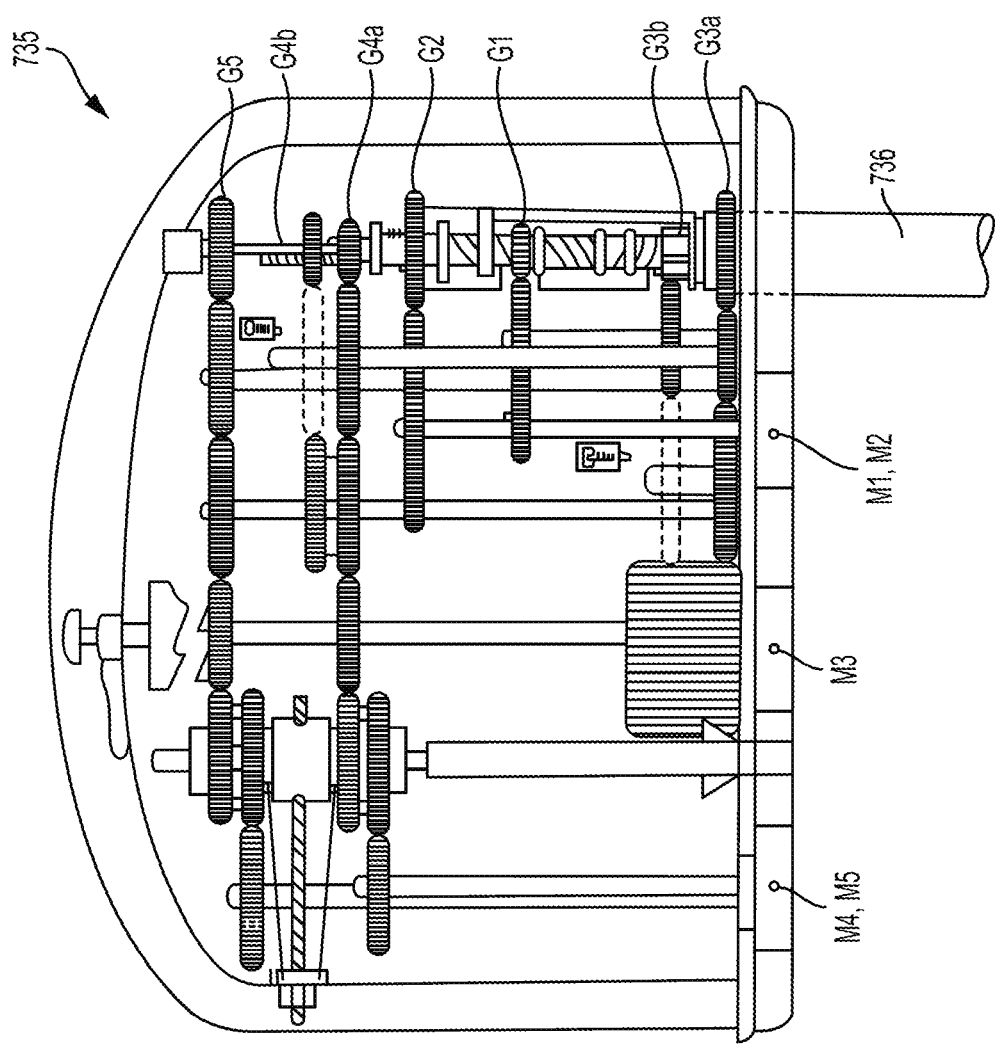
FIG. 5 illustrates an embodiment of a puck and a proximal end of a shaft extending from the puck.

FIG. 5 illustrates an embodiment of a puck 735 and a proximal end of a shaft 736 extending from the puck 735. As shown in FIG. 5, the puck 735 includes a plurality of actuation gears and gear shafts that can be either directly or indirectly controlled by any one of the motors 442 associated with the driver 440. For example, as shown in FIG. 5, the puck 735 is configured to couple to five motors at the locations indicated by reference numbers M1, M2, M3, M4, and M5. In this embodiment, puck 735 includes first and second articulation gears G1, G2 that are coupled respectively to the first and second motors M1, M2 via a series of one or more additional gears and shafts. Actuation of the first and second motors M1, M2 will rotate the articulation gears G1, G2, which in turn cause linear movement of an articulation cable in a proximal or distal direction to thereby cause articulation of the end effector 438 in desired left and right directions. The puck 735 also includes a shaft rotation gear G3a that is coupled to the third motor M3 via a series of one or more additional gears and shafts. Actuation of the third motor M3 will thus rotate the shaft rotation gear G3a thereby causing rotation of the shaft 436 of the tool assembly 430. The third motor M3 can also be configured to shift and to couple, via a series of one or more additional gears and shafts, to a head rotation gear G3b, which will cause rotation of the end effector 438 relative to the shaft 436. The puck 735 further includes a firm close gear G4a that is coupled to the fourth motor M4 via a series of one or more additional gears and shafts. Actuation of the fourth motor M4 will rotate the firm close gear G4a to cause linear translation of a drive screw to firmly close the jaws of the end effector 438. The puck 735 further includes a quick close gear G4b that can also couple to the fourth motor M4 via a series of one or more additional gears and shafts. When motor M4 is shifted into engagement with the quick close gear G4b, actuation of the fourth motor M4 will rotate the quick close gear G4b to cause linear translation of a quick close cable to quickly close the jaws of the end effector 438. Finally, the illustrated puck 735 includes a firing gear G5 that is coupled to the fifth motor M5 via a series of one or more additional gears and shafts. Actuation of the fifth motor M5 will rotate the firing gear G5, thereby driving a lead screw linearly to advance a sled through the end effector 438, as will be discussed in more detail below.

Figure 6:
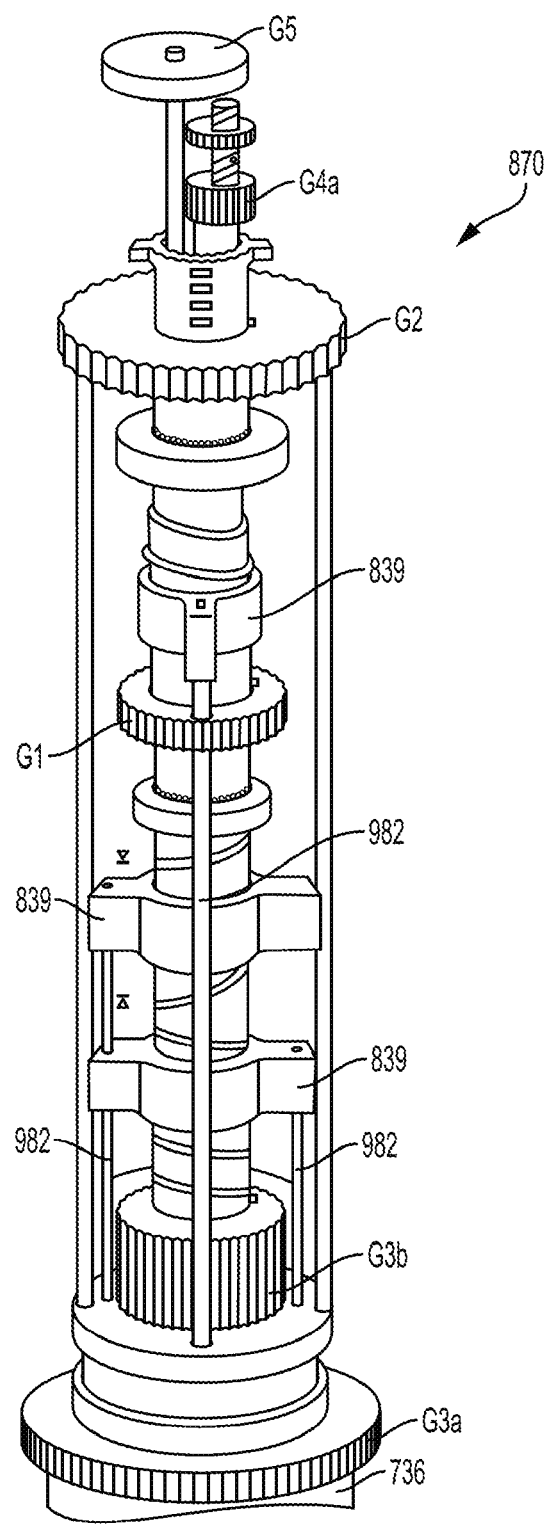
FIG. 6 illustrates an embodiment of the actuation assembly components of a puck.
Figure 7:
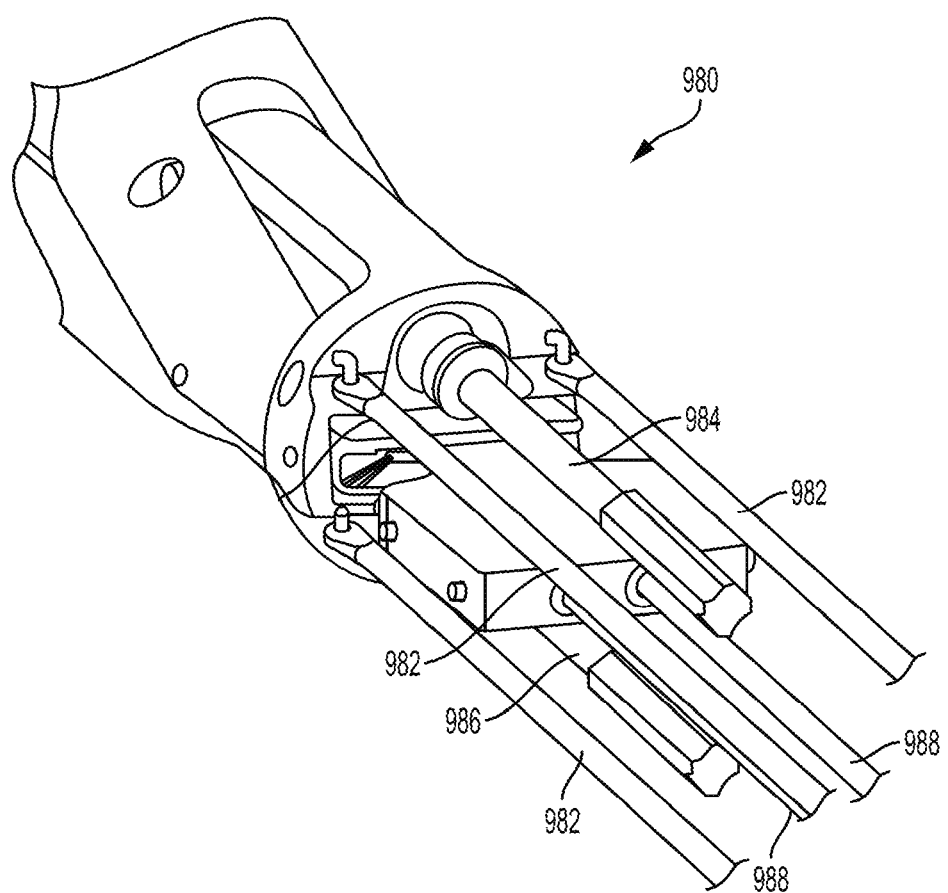
FIG. 7 illustrates a distal end of actuation shafts extending from a wrist located just proximal of an end effector.

FIG. 6 illustrates the actuation assembly 870 components of the puck of FIG. 5. As shown and indicated above, each of the gears G1-G5 is coupled to an actuation shaft that extends from the actuation assembly 870 and along the shaft 436 of the tool assembly 430, such as for controlling the movements of the end effector. FIG. 7 illustrates a distal end of the actuation shafts extending from a wrist 980 located just proximal of the end effector 438. The wrist 980 can allow for fine movements and angulation of the end effector 438 relative to the proximal end of the shaft 436. As shown in FIG. 7, the wrist 980 includes four articulation cables 982 that are spaced around a perimeter of the wrist 980. When actuated (e.g., pushed, pulled, rotated), the articulation cables 982 will cause articulation of the end effector 438 (e.g., movement up, down, left, right, and combinations thereof) relative to the proximal end of the shaft 436. The articulation cables 982 are connected to the articulation couplers 839, shown in FIG. 6, that are driven proximally and distally when the articulation gears G1, G2 are actuated by the first and second motors M1, M2. The wrist 980 also includes an upper rotary driver 984 that when actuated can cause the pair of jaws of the end effector 438 to firmly close. The upper rotary driver 984 is coupled to the firm close gear G4a shown in FIG. 6 such that rotation of the firm close gear G4a by the motor M4 causes rotation of the rotary driver 984. The wrist 980 can also include a lower rotary driver 986 that when actuated can cause movement of a sled located at the end effector 438. The lower rotary driver 986 is coupled to the firing gear G5 shown in FIG. 6 and it likewise rotates in response to rotation of the firing gear G5. The illustrated wrist 980 further includes a linear pull cable 988 that is coupled to the quick close gear G4b shown in FIG. 6 and that moves linearly in a proximal direction to cause rapid close of the pair of jaws.

Figure 8:
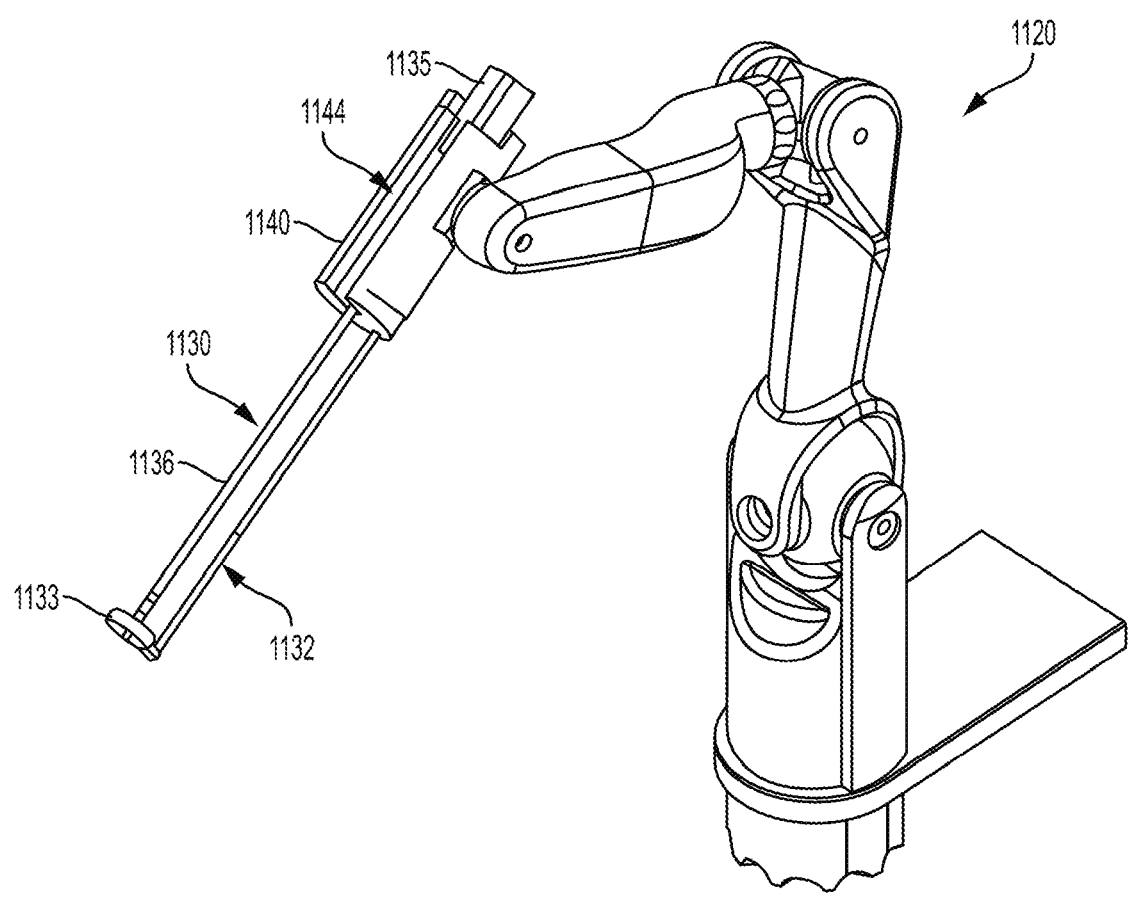
FIG. 8 illustrates an embodiment of a robotic arm and a tool assembly releasably coupled to the robotic arm.

FIG. 8 illustrates another embodiment of a robotic arm 1120 and a tool assembly 1130 releasably coupled to the robotic arm 1120. The robotic arm 1120 can support and move the associated tool assembly 1130 along one or more mechanical degrees of freedom (e.g., all six Cartesian degrees of freedom, five or fewer Cartesian degrees of freedom, etc.).

The robotic arm 1120 can include a tool driver 1140 at a distal end of the robotic arm 1120, which can assist with controlling features associated with the tool assembly 1130. The robotic arm 1120 can also include a movable tool guide 1132 that can retract and extend relative to the driver 1140.

A shaft of the tool assembly 1130 can extend parallel to a threaded shaft of the movable tool guide 1132 and can extend through a distal end feature 1133 (e.g., a ring) of the movable tool guide 1130 and into a patient.

In order to provide a sterile operation area while using the surgical system, a barrier (not shown) can be placed between the actuating portion of the surgical system (e.g., the robotic arm 1120) and the surgical instruments (e.g., the tool assembly 1130) in the sterile surgical field. A sterile component, such as an instrument sterile adapter (ISA), can also be placed at the connecting interface between the tool assembly 1130 and the robotic arm 1120. The placement of an ISA between the tool assembly 1130 and the robotic arm 1120 can ensure a sterile coupling point for the tool assembly 1130 and the robotic arm 1120. This permits removal of tool assemblies 1130 from the robotic arm 1120 to exchange with other tool assemblies 1130 during the course of a surgery without compromising the sterile surgical field.

Figure 9:
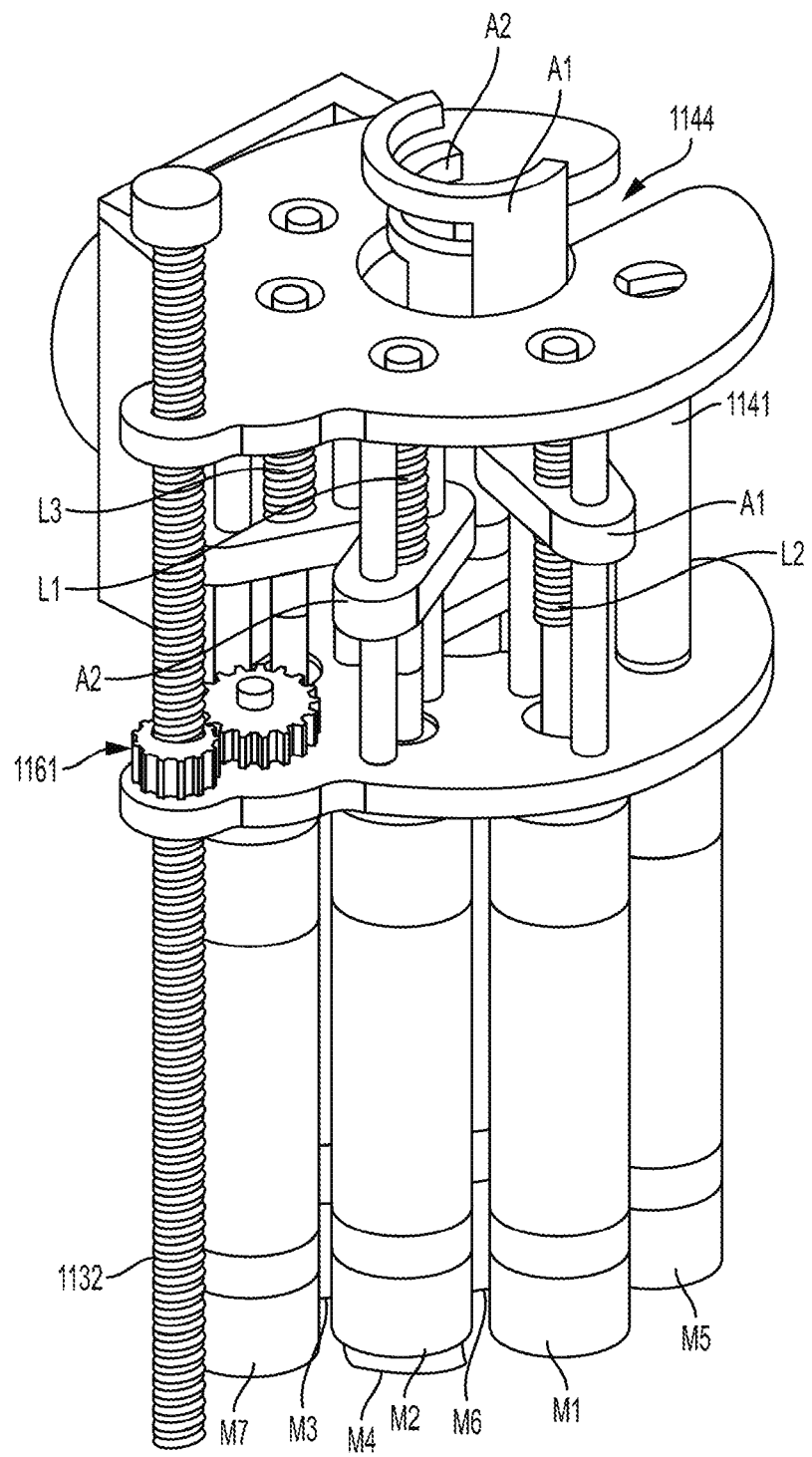
FIG. 9 illustrates an embodiment of a tool driver.

FIG. 9 illustrates the tool driver 1140 in more detail. As shown, the tool driver 1140 includes one or more motors, e.g., seven motors M1-M7 are shown, that control a variety of movements and actions associated with the tool assembly 1130, as will be described in greater detail below. The driver 1140 can also include one or more lead screws (e.g., three lead screws L1, L2, and L3 are shown) that can be individually rotated by a motor and, as a result of the rotation of the lead screw, cause linear and/or rotational movement of at least one actuator (e.g., see, for example, actuators A1 and A2 shown in FIG. 9). Movement of each actuator controls the movement of driving members (e.g., gears, cables) located in the tool assembly 1130 for controlling one or more actions and movements that can be performed by the tooling assembly 1130, such as for assisting with performing a surgical operation. The actuators extend from a top end of the driver 1140 for coupling to the driving members of the tool assembly 1130 mounted on top of the tool driver 1140.

The tool assembly 1130 can be loaded from a top side of the driver 1140 with the shaft of the tool assembly 1130 being positioned in a shaft-receiving channel 1144 formed along the side of the driver 1140. The shaft-receiving channel 1144 allows the shaft, which extends along a central axis of the tool assembly 1130, to extend along a central axis of the driver 1140 when the tool assembly 1130 is coupled to the driver 1140. In other embodiments, the shaft can extend through on opening in the tool driver 1140, or the two components can mate in various other configurations.

Figure 11:
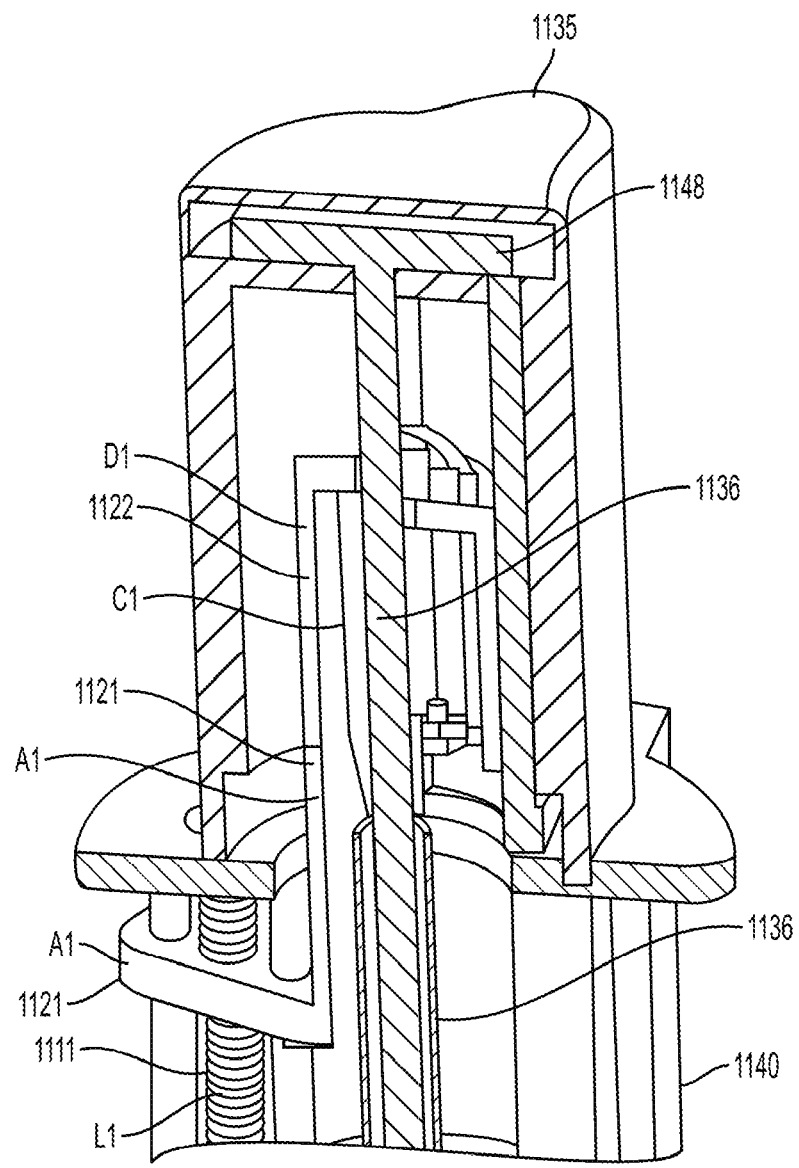
FIG. 11 illustrates an embodiment of a puck coupled to a driver with actuators extending from the driver into the puck and engaging driving member.

As shown in FIG. 11, the tool assembly 1130 includes a housing or puck 1135 coupled to a proximal end of a shaft 1136 and an end effector 1138 coupled to a distal end of the shaft 1136. The puck 1135 can include coupling features that assist with releasably coupling the puck 1135 to the tool driver 1140 of the robotic arm 1120. The puck 1135 can include driving members (e.g., gears, cables, and/or drivers) that can be directly or indirectly actuated by the one or more motors M1-M5, as will be described in greater detail below. The driving members in the puck 1135 can control the operation of various features associated with the end effector 1138 (e.g., clamping, firing, rotation, articulation, etc.), as well as control the movement of the shaft 1136 (e.g., rotation and/or articulation of the shaft).

The shaft 1136 can be releasably coupled to the puck 1135 such that the shaft 1136 can be interchangeable with other shafts. This can allow a single puck 1135 to be adaptable to various shafts 1136 having different end effectors 1138. The shaft 1136 can include actuators and connectors that extend along the shaft and assist with controlling the actuation and/or movement of the end effector 1138 and/or shaft 1136.

The shaft 1136 can also include one or more joints or wrists 1137 that allow a part of the shaft 1136 or the end effector 1138 to rotate and/or articulate relative to the longitudinal axis of the shaft 1136. This can allow for fine movements and various angulation of the end effector 1138 relative to the longitudinal axis of the shaft 1136. The end effector 1138 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 10:
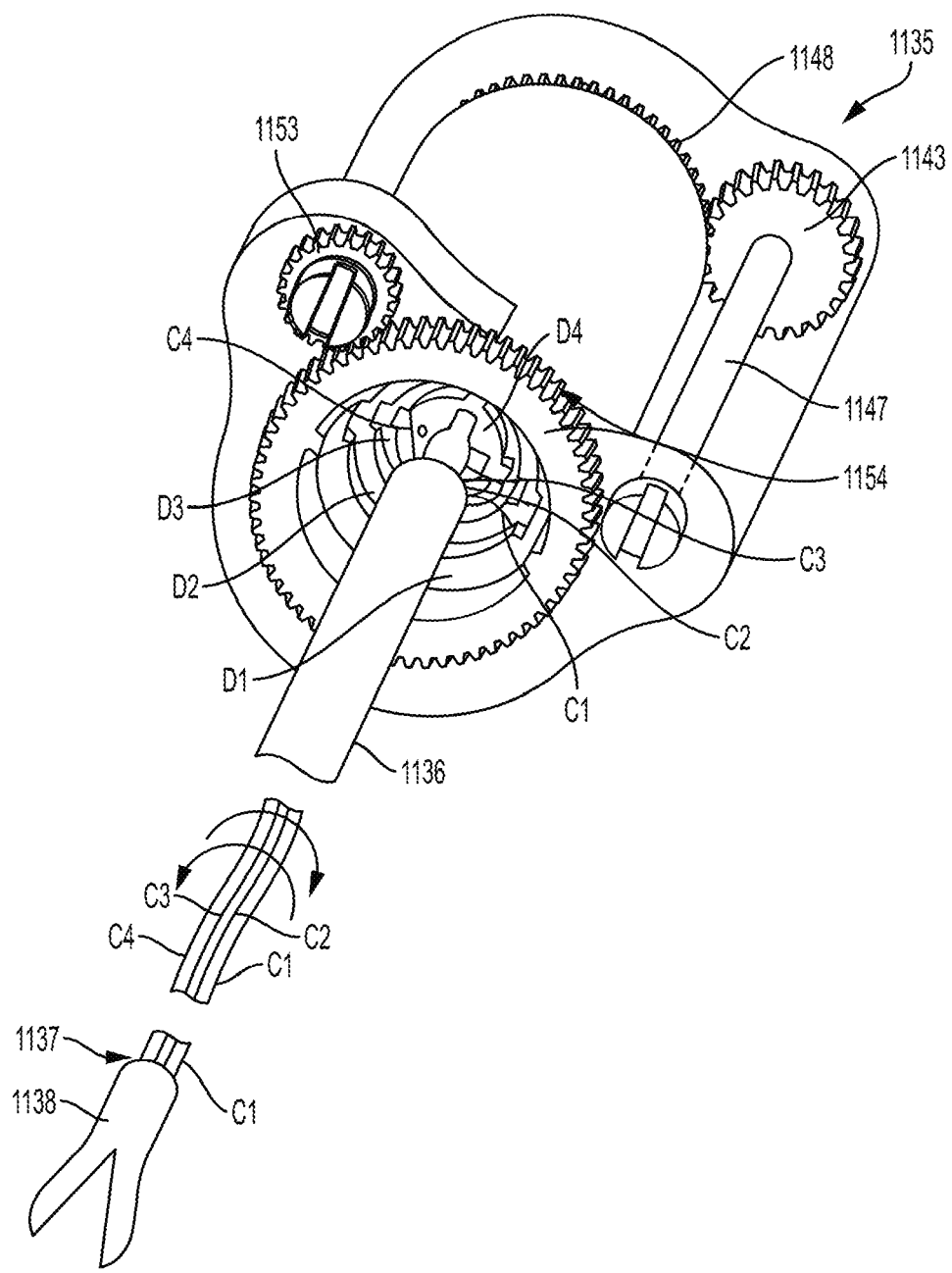
FIG. 10 illustrates a portion of a puck actuation assembly contained within a puck.

FIG. 10 illustrates a part of a puck actuation assembly contained within the puck 1135. As shown in FIG. 10, the puck 1135 includes at least one driving member (e.g., four driving members D1, D2, D3, and D4 are shown) that can each become engaged with an actuator of the driver 1140 such that actuation of an actuator causes actuation of a driving member thereby controlling the operation of various features associated with the shaft 1136 and/or end effector 1138. Each driving member D1-D4 can be coupled to a proximal end of a shaft or cable (e.g., four cables C1, C2, C3, and C4 are shown). Each cable can extend from a driving member and couple to a feature associated with either the shaft 1136 or the end effector 1138 thereby controlling a function of such feature.

FIG. 11 illustrates the puck 1135 coupled to the driver 1140 with the actuators extending from the driver 1140 into the puck 1135 and engaging the driving members. For example, motor M1 can cause lead screw L1 to rotate thereby causing actuator A1, which is threadably coupled to lead screw L1, to linearly advance in the proximal direction (towards and into the puck 1135). Actuator A1 can include an extension threadably coupled to the lead screw L1. The extension can be coupled to or integrated with a partial cylindrical shaft that extends along the longitudinal axis of the puck 1135 and the driver 1140. The partial cylindrical shaft of the actuator A1 can engage with driving member D1 such that when the actuator A1 is linearly advanced, the driving member D1 is caused to linearly advance in the same direction. Driving member D1 can be coupled to cable C1 such that when driving member D1 is advanced in the proximal direction, cable C1 is pulled in the proximal direction. Cable C1 extends along the shaft of the tool assembly 1130 and is operatively coupled to a part of the end effector 1138 thereby controlling a function of the end effector 1138 (e.g., opening and closing of jaws, deployment of a staple, etc.) when the cable is C1 translated in either the proximal or distal direction.

In some implementations, for example, four motors (e.g., M1-M4) can each individually control movement of a respective lead screw (e.g., L1-L4) thereby individually linearly translating a respective actuator (e.g., A1-A4) coupled thereto. Although the actuators are described as being linearly translated, the actuators can be linearly translated and/or rotationally moved as a result of actuation of a respective motor. Additional motors (e.g., motors M5 and M6) can be included in the driver 1140 for actuating various other aspects of the tool assembly 1130. For example, motor M5 can cause a first driver shaft 1141 to rotate, which is operatively coupled to a first puck shaft 1147 having a first puck gear 1143 coupled to a distal end of the first puck shaft 1147. Rotation of the first driver shaft 1141 thereby causes the first puck shaft 1147 and first puck gear 1143 to rotate. The first puck gear 1143 is engaged with a first shaft rotation gear 1148 that is caused to rotate as a result of the first puck gear 1143 rotating. The first shaft rotation gear 1148 is operatively coupled to the shaft 1136 of the tool assembly 1130 and can thereby cause rotation of the shaft 1136 and/or end effector 1138. Motor M6 can cause a second driver shaft to rotate, which is operatively coupled to a second puck gear 1153. The second puck gear 1153 is engaged with a second shaft rotation gear 1154 that is caused to rotate as a result of the second puck gear 1153 rotating. The second shaft rotation gear 1154 is also operatively coupled to the shaft 1136 and, upon rotation, provides additional torque through the shaft 1136 and for various features associated with the end effector 1138. Actuation of motor M7 can cause shaft gears 1161 to rotate, thereby causing the threaded shaft of the movable tool guide 1132 to linearly translate.

Terminology

Figure 12:
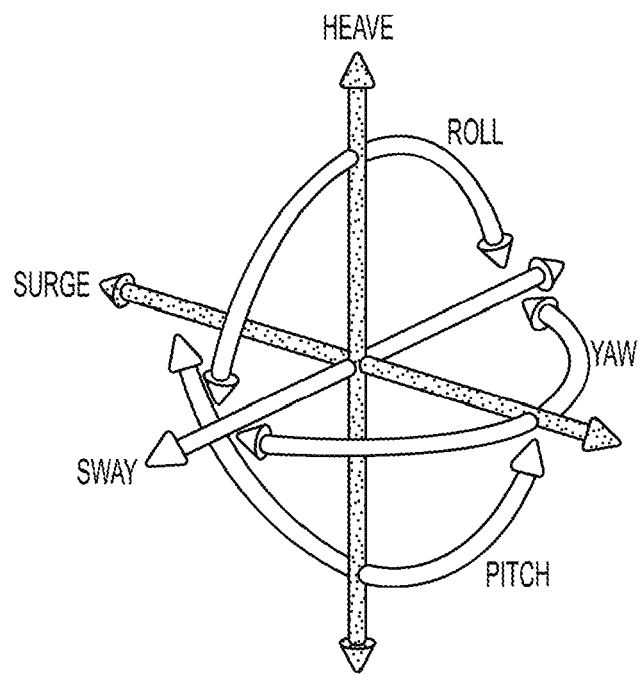
FIG. 12 illustrates the degrees of freedom of movement within a surgical robotic system.

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, and sway, and by the three rotational or orientation variables, e.g., Euler angles or roll, pitch, and yaw, that describe the position and orientation of a component of a surgical system with respect to a given reference Cartesian frame. As used herein, and as illustrated in FIG. 12, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientation variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes include various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 13:
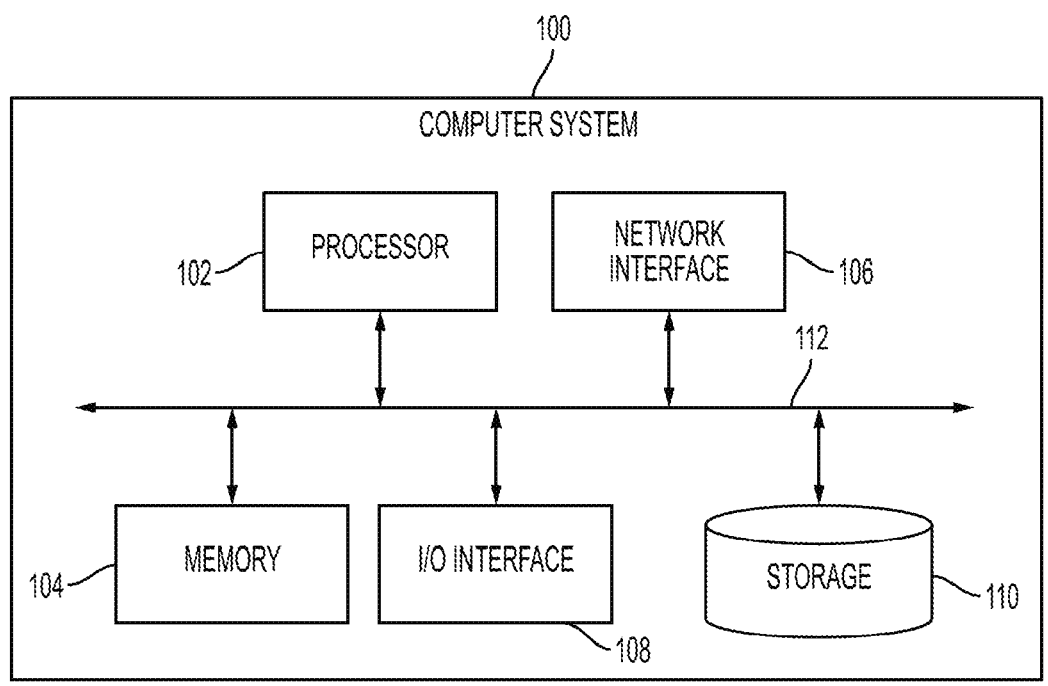
FIG. 13 illustrates an embodiment of a computer system.

FIG. 13 illustrates an embodiment of a computer system 100. As shown, the computer system 100 includes one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (JO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 13 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

In some embodiments, a robotic surgical system can include an electromechanical tool assembly (e.g., tool assembly 330 in FIG. 1 or tool assembly 430 in FIGS. 2-4) including a surgical instrument adapted to apply energy, such as ultrasonic and/or radiofrequency (RF) energy, to tissue held by the surgical instrument. The electromechanical tool is configured to be mounted on an electromechanical arm (e.g., robotic arm 320 in FIG. 1 or robotic arm 420 in FIG. 2) and it is configured to move with or relative to the electromechanical arm. The robotic surgical system further includes a controller operatively coupled to the electromechanical arm and the electromechanical tool and configured to control operation of these components.

The surgical instrument can be an end effector or other type of an instrument that can transmit one or more forms of energy (e.g., ultrasonic and/or RF) through tissue to cut and cauterize and seal the tissue. After the seal in tissue is created, application of energy to the tissue is discontinued and tissue is disengaged from the end effector. As discussed above, the proper cutting and sealing of tissue require delivery of an appropriate amount of energy to the tissue. In a typical, manual surgical procedure, a surgeon exercises subjective control over the movement of the surgical instrument, thereby affecting the amount of energy that is applied to the tissue. Failure to deliver a proper amount of energy by moving the surgical instrument at an improper speed (e.g., too fast or too slow) can lead to insufficient cutting or sealing (e.g., cold cut), or to unintended tissue damage if too much energy is applied to the tissue.

Accordingly, the robotic surgical system described herein can automatically control a level and/or form of energy that is applied to tissue during the treatment of tissue. The controller (and/or other suitable component(s) of the robotic surgical system) can be configured to receive, during an application of energy (e.g., ultrasonic and/or RF) to the tissue, a plurality of measurements indicative of a speed at which the surgical instrument is moving across or through the tissue. The parameters that indicate the speed at which the surgical instrument is being moved across or through tissue include tension that is being exerted against the surgical instrument by the tissue. A high level of tension generally indicates that the surgical instrument is being moved at a high speed. In addition, a high level of tension can also indicate certain tissue characteristics including, for example, that the tissue being treated is rough, stiff, and/or thick. In either case, a higher power may be required in order to ensure a proper cut and seal of the tissue. Thus, as discussed in more detail below, the controller can determine a speed at which the surgical instrument is being moved across or through tissue, and adjust a power that is being applied to the tissue accordingly. Moreover, the controller can further detect when a speed of movement exceeds a certain threshold thereby requiring introduction of an additional form of energy in order to proper cut and cauterize the tissue. In some example embodiments, the robotic surgical system can also monitor a temperature of the tissue in order to detect when to adjust the power being applied to the tissue in order to avoid applying an excessive amount of energy and damaging the tissue through overheating.

The robotic surgical system can be configured to control and adjust the level and/or forms of energy in any suitable way. For example, the surgical system can increase (or reduce) the power being applied and/or turn on an additional form of energy. Regardless of the specific way in which the surgical system adjusts energy, the surgical procedure as described herein may not be dependent on a surgeon's subjective control over the movement of the surgical instrument across or through tissue at a treatment site.

Figure 14A:
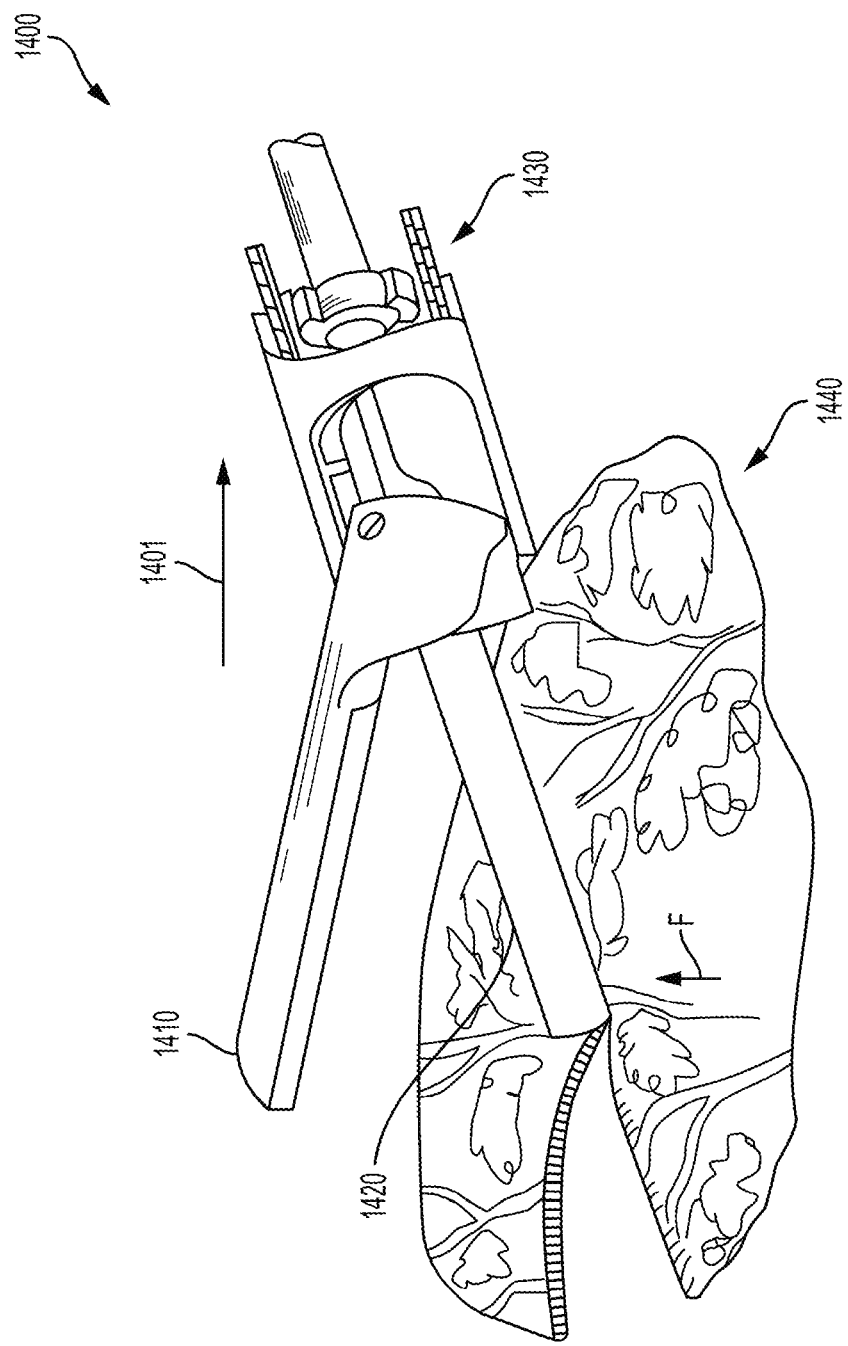
FIG. 14A illustrates an embodiment of an end effector.
Figure 14B:
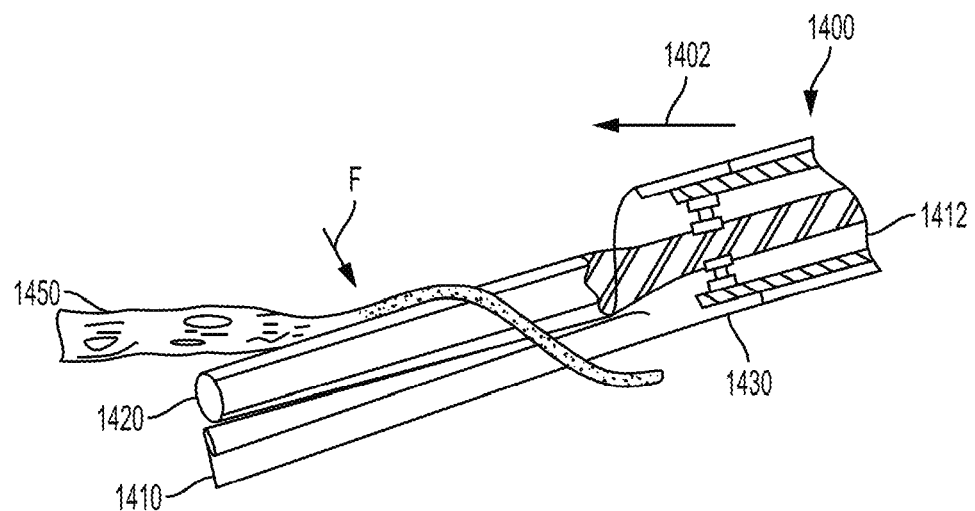
FIG. 14B illustrates a bend load caused by a force exerted against the end effector of FIG. 14A.
Figure 14C:
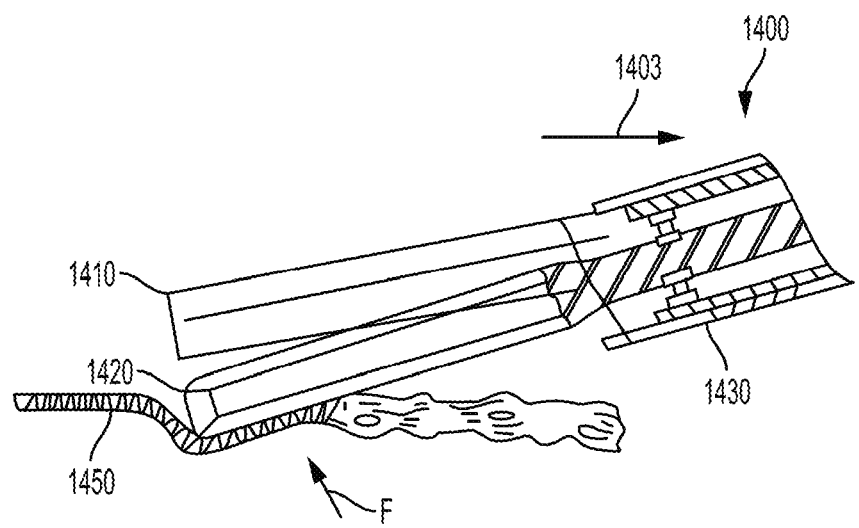
FIG. 14C illustrates a longitudinal load caused by a force exerted against the end effector of FIG. 14A.

FIGS. 14A-14C illustrate an embodiment of an end effector 1400 of a robotic surgical system in accordance with the disclosed techniques. The end effector 1400 is configured to cut and seal tissue by applying one or more forms of energy (e.g., ultrasonic and/or RF) thereto. The end effector 1400 can be positioned at a distal end 1412 of an instrument shaft of an electromechanical tool assembly (not shown), such as, for example, the tool assembly 330 (FIG. 1) or 430 (FIGS. 2-4). The tool assembly can be releasably mounted on an electromechanical robotic arm such as, for example, the robotic arm 320 (FIG. 1) or 420 (FIGS. 2 and 3). The end effector 1400 can be, for example, the end effector 438 (FIG. 4), or any other type of a surgical instrument configured to apply ultrasonic energy or other form of energy to tissue to cut and coagulate it. The tool assembly is configured to move relative to the electromechanical arm.

As shown in FIG. 14A, the end effector 1400 includes an upper jaw or a clamp member 1410 and a lower jaw or blade 1420 that are configured to clamp tissue therebetween or contact tissue in other ways. Thus, as shown in FIGS. 14A-14C, the end effector can also be moved over tissue with an outer surface of the blade 1420 positioned in contact with the tissue. The end effector can be advanced, dragged, or otherwise moved along the tissue to create a cut therethrough or other feature. The end effector also includes a strain gauge 1430 discussed in more detail below. Other components of the surgical system are not shown in FIGS. 14A-14C for the sake of simplicity.

The clamp member 1410 and the blade 1420 can have a variety of different configurations. The clamp member 1410 can have a tissue-facing surface configured (e.g., in shape and/or size) to grasp the tissue 1440 (or another type of tissue) between the clamp member 1410 and the blade 1420. The tissue-facing surface of the clamp member 1410 can have one or more surface features adapted to facilitate the grasping and securing of the tissue 1440 (or another type of tissue) between the clamp member 1410 and the blade 1420. The features formed on the tissue-facing surface can form one or more patterns or combination of patterns.

In some example embodiments, the blade 1420 can be configured to treat (e.g., cut and/or cauterize) the tissue 1440 when one or more forms of energy are applied thereto. For instance, the end effector 1400 can include a transmission element or waveguide (not shown separately) that is configured to transmit ultrasonic from an energy source to the blade 1420. The blade 1420 can be integral with the waveguide so as to form a single unit, or they can be separate elements connected to one another in a suitable way. Similarly, for a RF device, one or more electrodes can be present on upper and lower jaws 1410, 1420 (and any knife blade that may be present) so as to communicate energy between the electrodes and a suitable electrosurgical generator. Regardless of the configuration of the blade and the waveguide, the blade 1420 can be configured to transmit one or more forms of energy to tissue in order to treat the tissue in a controlled manner.

The described robotic surgical system can include an ultrasonic transducer coupled to an ultrasonic generator via a suitable transmission medium. The ultrasonic transducer can be coupled to the waveguide to transmit ultrasound signals thereto. It should be appreciated, however, that the described robotic surgical system can have other components configured to deliver ultrasound energy to the end effector 1400. Furthermore, the robotic surgical system can additionally include an RF generator coupled to a suitable source of RF energy. Regardless of the type, number, and configuration of such components, they can be controlled via a controller system, e.g., the control system 315 in FIG. 1, or any other controller(s).

The end effector 1400 can be configured to apply one or both ultrasound and RF energy to tissue. In some implementations, the end effector can have an isolated electrode on the lower jaw that provides energy to tissue and that is configured to provide a return path for either type of energy back to a generator. In implementations in which the end effector includes an ultrasonic blade, the movement of the end effector across tissue can be referred as "back cutting." A technique of "dragging" across tissue can be performed using monopolar blades and exposed ultrasonic blades. In some embodiments, an RF device can be used in the described manner a bipolar mode (i.e., the device includes two electrical poles or contacts). The RF device can have a tip configured to be used for both monopolar and bipolar cutting functions. A non-limiting example of such device is Enseal PowerTip (SurgRx, Inc.).

In some embodiments, the end effector 1400 can be adapted to sense one or more parameters including, for example, a force F exerted against the end effector 1400. FIG. 14A illustrates by way of example a position of the end effector 1400 when it is moved (e.g., dragged) along a tissue 1440 in a direction of an arrow 1401. In this example, as shown, the end effector 1400 is moved in the direction 1401 as the tissue 1440 is being cut such that the cut is created. The strain gauge 1430 can be configured to measure the force F exerted against the end effector 1400 (e.g., the blade 1420) by the tissue 1440. Specifically, the strain gauge 1430 is subjected to a bend load that corresponds to the force F exerted against the end effector 1400 (e.g., the blade 1420). In the illustrated example, the tissue 1440 is in the form of mesentery tissue. However, it should be appreciated that the tissue 1440 can be any other type of tissue without departing from the scope of the present disclosure.

FIG. 14B illustrates an example in which the end effector 1400 is moved (e.g., advanced) in a direction shown by an arrow 1402 to treat a vessel 1450 disposed over the blade 1420. In this example, the vessel 1450 causes a deformation strain or load in the form of a force F exerted against a distal end of the blade 1420. As in the example of FIG. 14A, the gauge 1430 measures this strain or load. Alternately or additionally, as shown in FIG. 14C, the strain gauge 1430 can measure a longitudinal load that corresponds to the force F exerted against the end effector 1400 (e.g., against the blade 1420). Thus, FIG. 14C illustrates an example in which the end effector 1400 is moved (e.g., dragged) in a direction shown by an arrow 1403 along the vessel 1450. In this example, the end effector 1400 experiences a longitudinal load caused by the force F exerted against the blade 1420 by the vessel 1450. It should be appreciated that the vessel 1450 is shown in FIGS. 14B and 14C by way of example only.

The force F can correspond to a tension across tissue, such as the tissue 1440 (FIG. 14A) or the vessel 1450 (FIGS. 14B and 14C). For example, when the tissue is rough, stiff, and/or thick, the tissue can exhibit high tension and therefore present greater resistance against the movement of the blade 1420 through the tissue. Thus, the magnitude of the force F can be indicative of one or more characteristics of the tissue including, for example, the roughness, stiffness, and/or thickness of the tissue. In addition, the force F can also correspond to a velocity of the end effector 1400 (e.g., the blade 1420) through the tissue. For instance, the blade 1420 can encounter greater resistance from the tissue when the end effector 1400 is being moved (e.g., advanced or dragged) quickly (e.g., by the robotic arm 200) through the tissue. Thus, the magnitude of the force F can also be indicative of a speed of the movement of the end effector 1400 through the tissue.

In some embodiments, the end effector 1400 can be adapted to apply, to the tissue 1440, RF energy, ultrasonic energy, and/or a combination of both. The level and/or forms of energy (e.g., RF and/or ultrasonic) applied by the end effector 1400 can be controlled by the control system 115 based on the parameters sensed by the end effector 1400. According to some embodiments, the level and/or forms of energy applied by the end effector 1400 can be adjusted based on the force F exerted against the end effector 1400 (e.g., the blade 1420) by the tissue 1440. For example, the control system 115 can increase the power and/or combine the different types of energies (e.g., combination ultrasonic and RF) applied by the end effector 1400 when the force F indicates that the tissue 1440 is rough, stiff, and/or thick. Alternately or additionally, the control system 115 can increase the power and/or combine the different types of energies applied by the end effector 1400 when the force F indicates that the end effector 1400 is being moved (e.g., advanced or dragged) quickly (e.g., by the robotic arm 200) through the tissue 1440.

FIGS. 15A-15D illustrate an embodiment of an end effector 1500 of a robotic system in accordance with the disclosed techniques. Other components of the surgical system are not shown in FIGS. 15A-15D for the sake of simplicity. The end effector 1500 is adapted to cut and seal tissue by applying one or more forms of energy (e.g., RF) thereto. The end effector 1500 can be positioned at a distal end 1512 of an instrument shaft of an electromechanical tool assembly (not shown), such as, for example, the tool assembly 330 (FIG. 1) or 430 (FIGS. 2-4). The tool assembly can be releasably mounted on an electromechanical robotic arm such as, for example, the robotic arm 320 (FIG. 1) or 420 (FIGS. 2 and 3). The end effector 1500 can be, for example, the end effector 438 (FIG. 4), or any other type of a surgical instrument configured to apply one or more forms of energy to tissue to cut and coagulate it. The tool assembly is configured to move relative to the electromechanical arm.

Figure 15A:
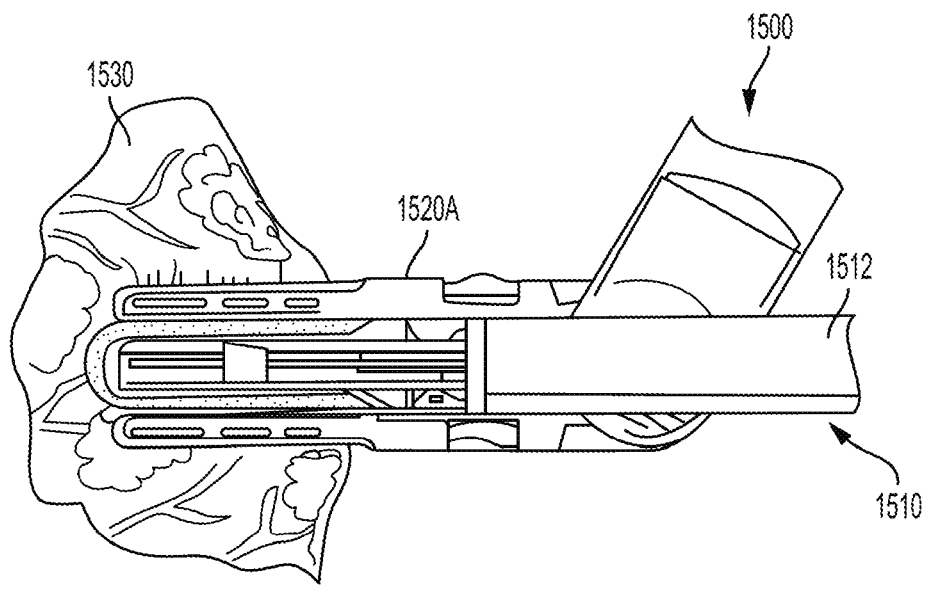
FIG. 15A illustrates a top view of an embodiment of an end effector.

FIG. 15A illustrates a top view of the end effector 1500. As shown, the end effector 1500 can include an RF device 1510 adapted to provide RF energy. The end effector 1500 can also be configured to deliver ultrasound energy to tissue, in which case it includes components required to generate and deliver to the ultrasound energy to tissue. The end effector 1500 can further include a grasper 1520, which can include an upper grasper member 1520A and a lower grasper member 1520B. According to some embodiments, the end effector 1500 can apply RF energy (e.g., from the RF device 1510) to a tissue 1530 while the tissue 1530 is secured by the grasper 1520 (e.g., between the upper grasper member 1520A and the lower grasper member 1520B). It should be appreciated that the tissue 1530 can be any type of tissue (e.g., blood vessel, organ) without departing from the scope of the present disclosure.

The grasper 1520 can have a variety of configurations. The upper grasper member 1520A and/or the lower grasper member 1520B can have a tissue-facing surface configured (e.g., in shape and/or size) to grasp and secure the tissue 1530 between the upper grasper member 1520A and the lower grasper member 1520B. The tissue-facing surface of the upper grasper member 1520A and/or the lower grasper member 1520B can have one or more surface features adapted to facilitate the grasping and securing of the tissue 1440. These features can form one or more patterns or combination of patterns.

Figure 15B:
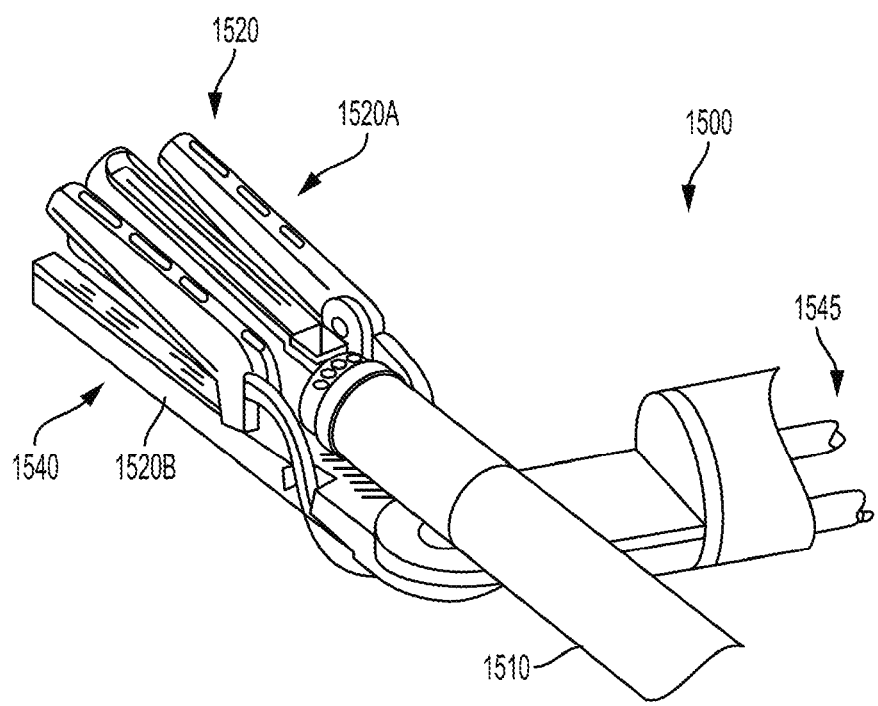
FIG. 15B illustrates a perspective view of the end effector of FIG. 15A.

FIG. 15B illustrates a perspective view of the end effector 1500. Referring to FIGS. 15A and 15B, the end effector 1500 can further include a cooling element 1540 and cooling tubes 1545. The cooling element 1540 can be disposed on the lower grasper member 1520B of the grasper 1520. In some embodiments, the cooling element 1540 can be a Peltier cooler adapted to provide thermoelectric cooling to the tissue 1530 while the tissue 1530 is treated with RF energy from the RF device 1510. It should be appreciated, however, that any type of cooling element can be used as the described techniques are not limited in this respect.

Figure 15C:
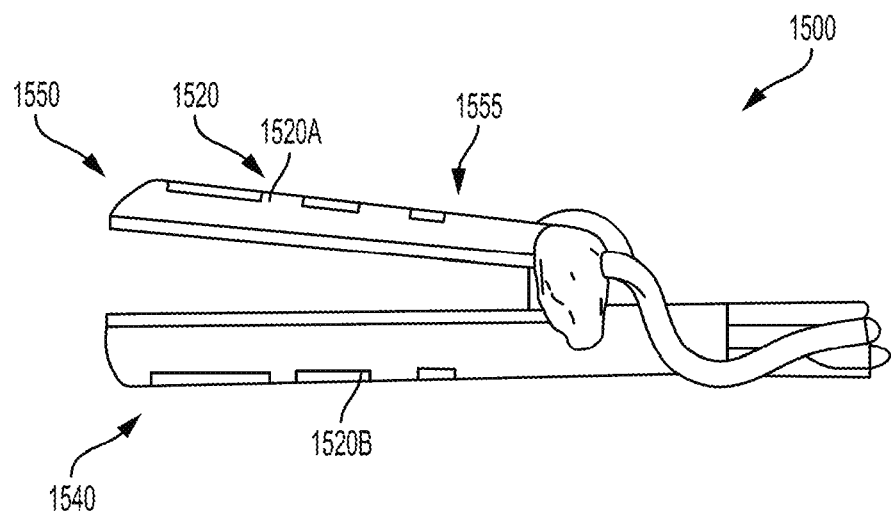
FIG. 15C illustrates a side view of an embodiment of the end effector of FIG. 15A.

FIG. 15C illustrates schematically a side view of the end effector 1500. Referring to FIGS. 15A-15C, the end effector 1500 can further include a plurality of sensors including, for example, a first sensor 1550 and a second sensor 1555. As shown in FIG. 15C, the first sensor 1550 can be positioned at a distal end of the upper grasper member 1520A while the second sensor 1550 can be positioned at a proximal end of the upper grasper member 1520B. In some embodiments, the first sensor 1550 and the second sensor 1555 can be temperature sensors adapted to measure a temperature of the tissue 1530 while the tissue 1530 is treated with RF energy from the RF device 1510. It should be appreciated that two sensors 1550, 1555 are shown by way of example only and that the end effector 1500 can include any suitable number of sensors, without departing from the scope of the present disclosure. Furthermore, the end effector can include other type(s) of sensors.

In some embodiments, the end effector 1500 can be adapted to apply RF energy (e.g., from the RF device 1510) to the tissue 1530. The rate of power provided by the RF device 1510 and applied by the end effector 1500 can be controlled by the control system 115 based on the parameters sensed by the end effector 1500 including, for example, the temperature at the tissue 1530. For example, the control system 115 can decrease the rate of the RF energy when the temperature at the tissue 1530 is high. Also, the control system 115 can increase the rate of RF energy when the temperature at the tissue 1530 is low. Thus, the control system 115 can be configured to adjust the power by increasing the power when the temperature of the tissue is below a first threshold value and decreasing the power when the temperature of the tissue is above a second threshold value. The first and second threshold values can be selected based on a number of parameters, such as a type of tissue, type of surgery and/or any other suitable factors. Controlling the rate of RF energy applied to the tissue 1530 based on the temperature at the tissue 1530 can ensure that an adequate amount of RF energy is applied to the tissue 1530 while preventing overheating and damage to the tissue 1530.

Figure 15D:
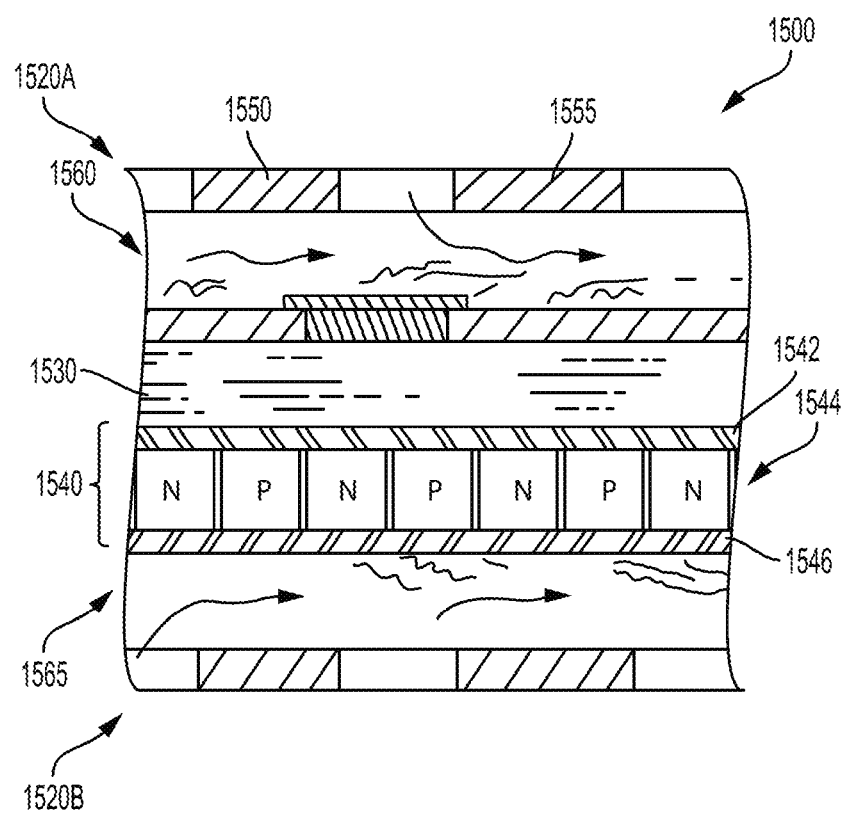
FIG. 15D illustrates a cross sectional view of the end effector of FIG. 15A.

FIG. 15D illustrates a cross sectional view of the end effector 1500. As shown, the tissue 1530 can be secured between the grasper 1520 (e.g., the upper jaw 1520A and the lower jaw 1520B) in order to be treated with RF energy from the RF device 1510. As shown in FIG. 15D, the upper jaw 1520A can include a first air space 1560 while the lower jaw 1520B can include a second air space 1565. The first and second air spaces 1560, 1565 (which are referred to as "first" and "second" for description purposes only) can be adapted to provide insulation.

The cooling element 1540 can be adapted to maintain a temperature of the tissue 1530 while the tissue 1530 is treated with RF energy (e.g., from the RF device 1510). As shown in FIG. 15D, the cooling element 1540 can include a hot plate 1542 and a cold plate 1546. The cooling element 1540 can further include an interconnect 1544 (e.g., a layer of n-type and p-type semiconductors) disposed between the hot plate 1542 and the cold plate 1546. In some embodiments, the cold plate 1546 can absorb at least a portion of the heat applied to the tissue 1530 (e.g., by the RF device 1510) and transfer the heat to the hot plate 1542 via the interconnect 1544. This transfer of heat allows the cold plate 1546 to remain cool and to continue cooling the tissue 1530 while the tissue 1530 is treated with RF energy.

Figure 16A:
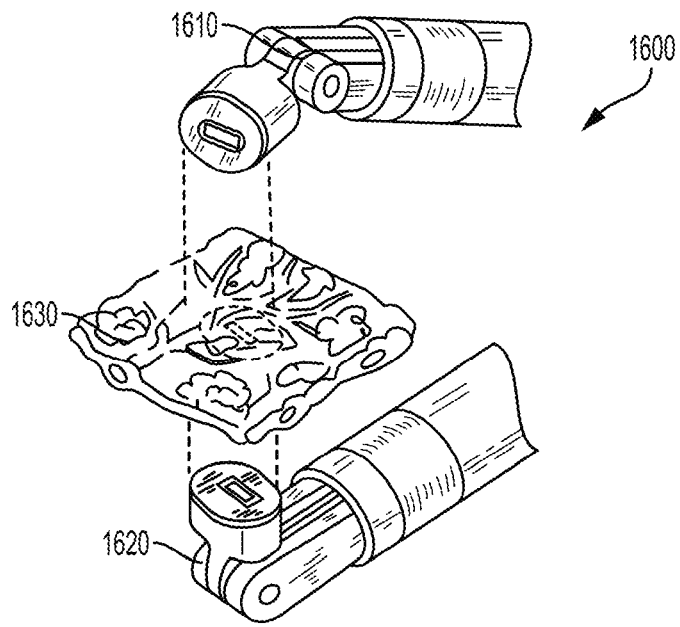
FIG. 16A illustrates an embodiment of an end effector.

FIG. 16A illustrates another example of a portion of an end effector 1600 of a robotic surgical system in accordance with the disclosed techniques. Only a distal end of the end effector 1600 is shown, and other components of the surgical system are not shown in FIG. 16A for the sake of simplicity. The end effector 1600 is adapted to seal tissue by applying one or more forms of energy (e.g., ultrasonic and/or RF) thereto. The end effector 1600 can be positioned at a distal end of an instrument shaft of an electromechanical tool assembly (not shown), such as, for example, the tool assembly 330 (FIG. 1) or 430 (FIGS. 2-4). The tool assembly can be releasably mounted on an electromechanical robotic arm such as, for example, the robotic arm 320 (FIG. 1) or 420 (FIGS. 2 and 3). The end effector 1600 can be, for example, the end effector 438 (FIG. 4), or any other type of a surgical instrument configured to apply one or more forms of energy to tissue to cut and coagulate it. The tool assembly is configured to move relative to the electromechanical arm.

As shown in FIG. 16A, the end effector 1600 can be a bipolar welder having a first arm 1610 and a second arm 1620. The end effector 1600 can apply one or more forms of energy (e.g., RF, ultrasonic) to a tissue 1630 positioned between the first arm 1610 and the second arm 1620. The tissue 1630 can be any type of tissue (e.g., blood vessel, organ) without departing from the scope of the present disclosure.

Figures 16B, 16C, 16D:
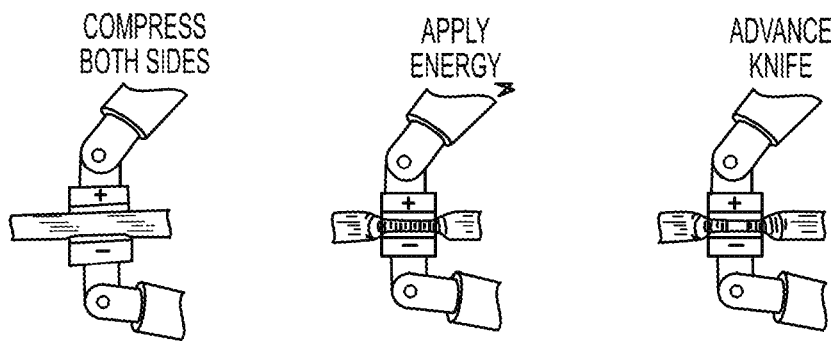
FIGS. 16B-16D are schematic views illustrating an example of a sequence of operations of the end effector of FIG. 16A.
Figure 16E:
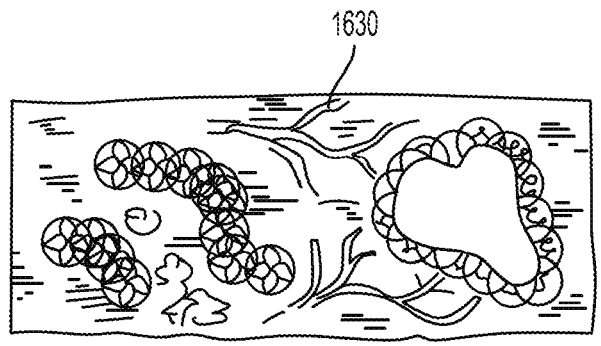
FIG. 16E is a schematic view illustrating an example of patterns that can be created by an end effector.

FIGS. 16B-16D illustrate an example of a sequence of operations of an embodiment of an end effector, such as the end effector 1600 in FIG. 16A. As shown in FIG. 16B, a portion of tissue (e.g., the tissue 1630) can be compressed between first and second arms of an end effector (e.g., arms 1610, 1620 of the end effector 1600). As shown in FIG. 16C, the end effector 1600 can apply one or more forms of energy (e.g., RF, ultrasonic) to that portion of the tissue 1630 while it is compressed between the first arm 1610 and the second arm 1620. The end effector 1600 can subsequently be advanced to a different (e.g., adjacent) portion of the tissue 1630, as shown in FIG. 16D. In this way, the end effector 1600 can spot weld and/or seal and cut the tissue 1630 to create various patterns, examples of which are shown in FIG. 16E.

In some embodiments, the end effector 1600 can be configured to sense one or more parameters including, for example, a tension of the tissue 1630 and/or a velocity at which the first arm 1610 is brought towards the second arm 1620. The level and/or type of energy applied by the end effector 1600 can be controlled by the control system 115 based on the parameters sensed by the end effector 1600.

Figure 17A:
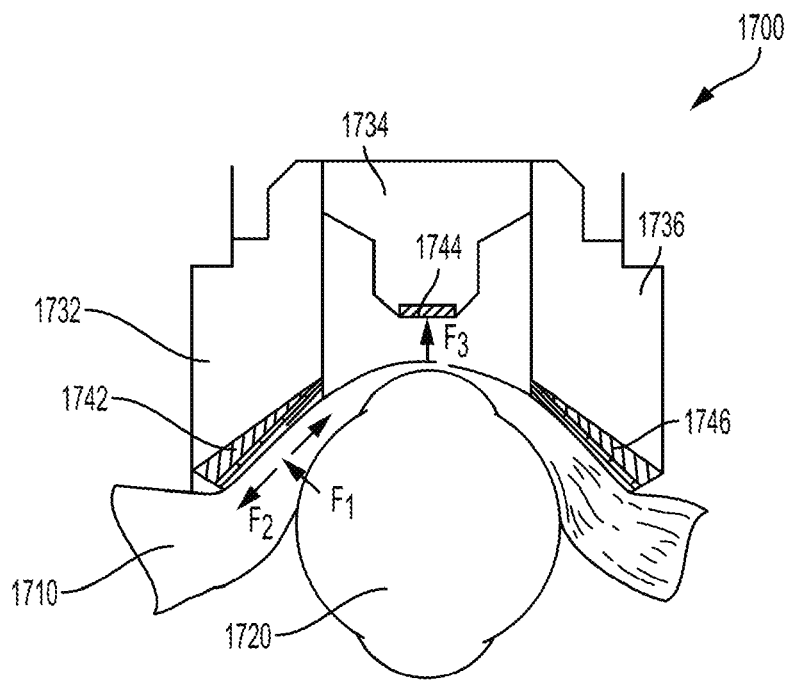
FIG. 17A illustrates a cross sectional view of an embodiment of an end effector.
Figure 17B:
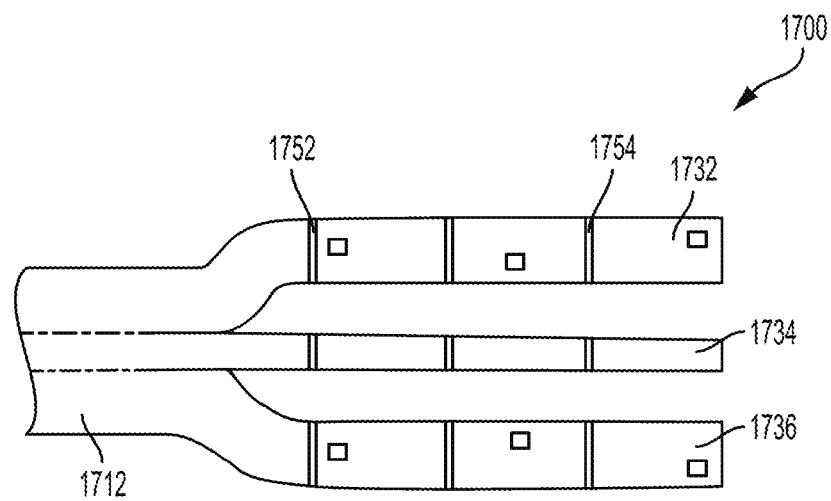
FIG. 17B illustrates a top view of an embodiment of an end effector.

FIGS. 17A-B illustrate an embodiment of an end effector 1700 of a robotic surgical system in accordance with the disclosed techniques. Other components of the surgical system are not shown in FIGS. 17A-B for the sake of simplicity. The end effector 1700 is adapted to cut and seal tissue by applying one or more forms of energy (e.g., ultrasonic, RF) thereto. The end effector 1700 can be positioned at a distal end 1712 of an instrument shaft of an electromechanical tool assembly (not shown), such as, for example, the tool assembly 330 (FIG. 1) or 430 (FIGS. 2-4). The tool assembly can be releasably mounted on an electromechanical robotic arm such as, for example, the robotic arm 320 (FIG. 1) or 420 (FIGS. 2 and 3). The end effector 1700 can be, for example, the end effector 438 (FIG. 4), or any other type of a surgical instrument configured to apply ultrasonic energy or other form of energy to tissue to cut and coagulate it. The tool assembly is configured to move relative to the electromechanical arm.

FIG. 17A illustrates a cross sectional view of the end effector 1700. As shown in FIG. 17A, the end effector 1700 can include a waveguide 1720. The waveguide 1720 can be adapted to propagate ultrasonic energy. The end effector 1700 can further include a set of clamp members including, for example, a first clamp member 1732, a second clamp member 1734, and a third clamp member 1736. The end effector 1700 can be adapted to apply ultrasonic and/or RF energy to the tissue 1710 when the tissue 1710 is secured between the waveguide 1720 and the first clamp member 1732, the second clamp member 1734, and the third clamp member 1736.

In some embodiments, the end effector 1700 can be configured to sense one or more parameters including, for example, electrical impedance, force, and temperature. As shown in FIG. 17A, the first clamp member 1732, the second clamp member 1734, and the third clamp member 1736 can include sensors adapted to measure the forces exerted by the tissue 1710 against the end effector 1700 (e.g., a first force sensor 1742, a second force sensor 1744, and a third force sensor 1746). For example, the tissue 1710 can exert both longitudinal forces (e.g., the forces $F_1$ and $F_3$) and traverse forces (e.g. the force $F_2$) against the end effector 1700. As such, the first force sensor 1742, the second force sensor 1744, and the third force sensor 1746 can be adapted to measure the longitudinal and/or traverse forces exerted by the tissue 1710.

FIG. 17B illustrates a top view of the end effector 1700. As shown in FIG. 17B, the end effector 1700 can further include a plurality of temperature sensors including, for example, a first temperature sensor 1752 and a second temperature sensor 1754. In some embodiments, the first temperature sensor 1752 and the second temperature sensor 1754 can be adapted to measure a temperature of the tissue 1710 while the tissue 1710 is treated with RF and/or ultrasonic energy. The first temperature sensor 1752 and the second temperature sensor 1754 can be disposed along the first clamp member 1732. Additional temperature sensors can be disposed along the first clamp member 1732, the second clamp member 1734, and/or the third clamp member 1736 without departing from the scope of the present disclosure.

In some embodiments, the level and/or forms of energy (e.g., RF, ultrasonic) applied by the end effector 1700 can be controlled based on the parameters sensed by the end effector 1700 including, for example, electrical impedance, force, and temperature. For example, the forces (e.g., the forces $F_1$, $F_2$, and $F_3$ shown in FIG. 17A) exerted by the tissue 1710 against the end effector 1700 can be indicative of tissue characteristics including, for example, the roughness, stiffness, and/or thickness of the tissue 1710. The forces exerted by the tissue 1710 can further be indicative of a velocity of the movement (e.g., advancement, drag) of the end effector 1700 through the tissue 1710. Thus, based on the forces exerted by the tissue 1710 against the end effector 1700, the control system 115 can increase (or decrease) a rate of power applied by the end effector 1700. Alternately or additionally, the control system 115 can change the forms of energy applied by the end effector 1700. For example, the control system 115 can cause a combination of RF and ultrasonic energy to be applied by the end effector 1700 when the forces (e.g., the forces $F_1$, $F_2$, and $F_3$) sensed by the end effector 1700 indicate that the tissue 1710 is rough, stiff, or thick, and/or when the forces sensed by the end effector 1700 indicate that the end effector 1700 is being moved (e.g., advanced, dragged) quickly through the tissue 1710.

Figure 18A:
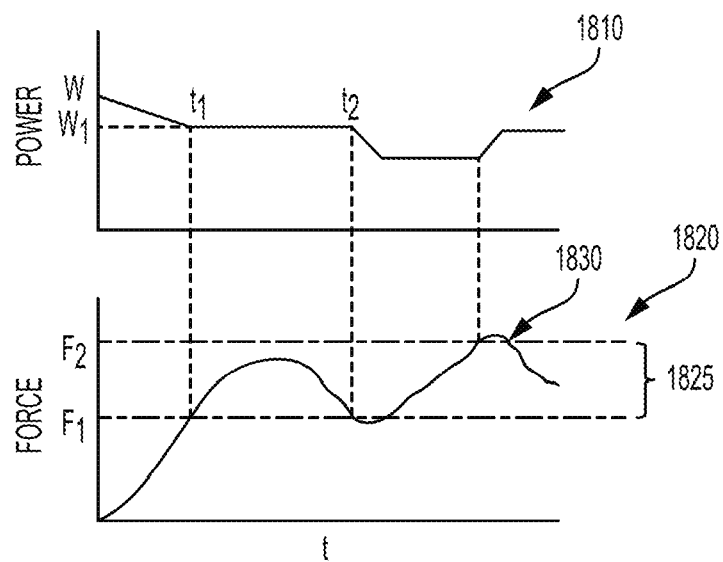
FIG. 18A illustrates graphs showing power adjustments when treating tissue with one or more forms of energy.

FIG. 18A illustrates examples of a power curve 1810 and a corresponding force curve 1820. Referring to FIG. 18A, the power curve 1810 depicts varying rates of power (or energy), expressed in watts, that can be applied to a tissue (or vessel) at various times t. The end effector is described herein as applying to power (or energy) to tissue. However, it should be appreciated that, while power is described, voltage and/or current can also be used to control operation of the end effector. In the case of the ultrasonic portion of the end effector, various frequencies and wave shapes can be used to control operation of the end effector.

A corresponding amount of tension present in the tissue (or vessel) is shown in the force curve 1820. In some embodiments, the force exerted by the tissue (e.g., against an end effector applying the energy) can correspond to the tension present in the tissue. The force exerted by the tissue can further correspond to a velocity at which the end effector moves (e.g., advances, drags) through the tissue. Thus, as shown in FIG. 18A, the power applied to the tissue can be adjusted based on measured force exerted by the tissue.

FIG. 18A shows that as the force exerted by the tissue (e.g., against the end effector applying the energy) increases from a zero value to a certain higher value, power (W) delivered to the tissue by the end effector also increases. In this example, this increase continues until a first threshold force value $F_1$ is reached, which corresponds to power W1 applied to the tissue. As shown, at this point, the force is within an acceptable force range 1825, which is a range between the first threshold force value $F_1$ and a second threshold force value $F_2$. While the force values, which can vary, stay within this range, the power applied to tissue remains constant. Thus, as shown, the power does not vary during a time period between a first time $t_1$ and a second time $t_2$. However, when the force exerted by the tissue is below the first threshold force value $F_1$, indicating that a thinner portion of tissue is being treated and/or that the end effector does not move sufficiently (e.g., by advancing, dragging, etc.) fast, the power can be decreased. Thin tissue is easier to cut than thick tissue. Thus, on thin tissue, the end effector can move faster and/or have less force exerted on it. For this reason, when the tissue is thin and/or the force is low, the power can be decreased.

As the force increases such that it is again within the acceptable force range 1825, the power (which has been decreased) remains constant. Further, when the force exerted by the tissue exceeds the second threshold force value $F_2$, (1830 in FIG. 18A), indicating that there may be an excessive amount of tissue and/or the end effector may be moving (e.g., advancing, dragging, etc.) too slow, the power can be increased, as shown in FIG. 18A. In this way, when the force exerted on the end effector is below or above certain values (in this example, the first and second thresholds $F_1$, $F_2$), the power is adjusted by being decreased or increased accordingly.

The first and second threshold values $F_1$, $F_2$ can be selected in many different ways. For example, they can be selected based on a type of tissue, a type of surgical procedure, patient's characteristics, and/or any other suitable factors. Also, a manner in which power values are adjusted based on the measured force values can vary based on various factors. For example, a change of power can be determined by the delta between the measured force and the threshold force value. A larger delta can require a more significant change in power. Power can be adjusted in a stepwise manner or in a linear manner. In some embodiments, a proportional or other mathematical relationship between the power rate and the force can be used. Minimum and maximum thresholds can also be set on power to ensure the desired tissue effect is achieved. Velocity can alter the change in power, as well as an indication (e.g., a signal) that counter traction is being applied by a second device. Power can also be varied depending on a time period during which the device has been activated. For example, the power level may not change regardless of force for the initial time period, until tissue effects start to occur (e.g., 500 milliseconds (ms), or any other suitable time period). Furthermore, in implementations in which a temperature sensor is used, a maximum allowed power (e.g., the "power cap") can be decreased so as to limit end effector temperature. Power adjustments and "power caps" can be specific to the instruments in use, the tissue temperature or end effector temperature and the history of various interactions of instruments and tissue during a surgical procedure.

In some embodiments, applying one type of energy (e.g., RF or ultrasonic energy alone) may not be adequate to thoroughly cut and cauterize the tissue. Thus, an additional type of energy may be introduced (e.g., a combination RF and ultrasonic) in order to ensure that an adequate amount of energy is applied to cut and cauterize the tissue. As mentioned above, an end effector in accordance with the described techniques can be configured to apply one type of energy, or it can be a combination device configured to apply (simultaneously or separately) two or more types of energy to tissue. For example, the end effector can configured to apply ultrasound and RF energy to tissue, and the described techniques can be used to acquire tissue parameters to determine when, and with which magnitude, one or both ultrasound and RF energy are to be applied to tissue.

Figure 18B:
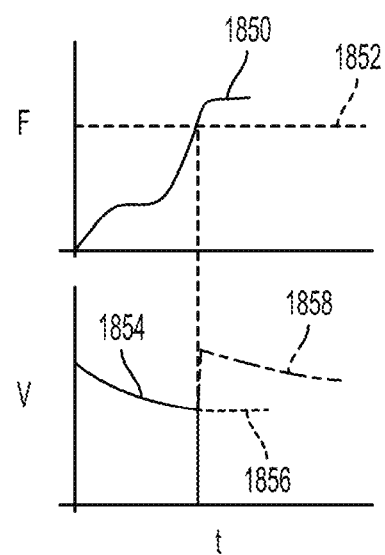
FIG. 18B illustrates graphs showing adjustments of energy types while treating tissue with one or more forms of energy.

FIG. 18B illustrates examples of a force curve 1850 and corresponding voltage curves for different forms of energy. As shown in FIG. 18B, a first voltage curve 1854 corresponds to the application of RF energy, a second voltage curve 1856 corresponds to the application of ultrasonic energy, and a third voltage curve corresponds to the application of both RF and ultrasonic energy.

The forces exerted by the tissue against an end effector adapted to apply ultrasonic energy (e.g., a waveguide in the end effector) can be subject to a force limit F, which corresponds to the force limit line 1852. For instance, the forces exerted against an ultrasonic end effector can exceed the force limit F when the end effector is encountering an excessively large amount of tissue and/or when the end effector is being moved (e.g., advanced, dragged) too quickly (e.g., by a surgeon). As such, applying ultrasonic energy alone (e.g., as represented by the second voltage curve 1856) may not be adequate to thoroughly cut and cauterize the tissue. Similarly, RF energy along (e.g., as represented by the first voltage curve 1854) also may not provide sufficient energy to cut and cauterize the tissue. Accordingly, as shown in FIG. 18B, both RF and ultrasonic energy may be applied to treat the tissue. The combined voltage of RF and ultrasonic energy is represented by the third voltage curve 1858. The combination of RF and ultrasonic energy can provide a sufficient amount of energy to cut and cauterize the tissue.

Figure 19:
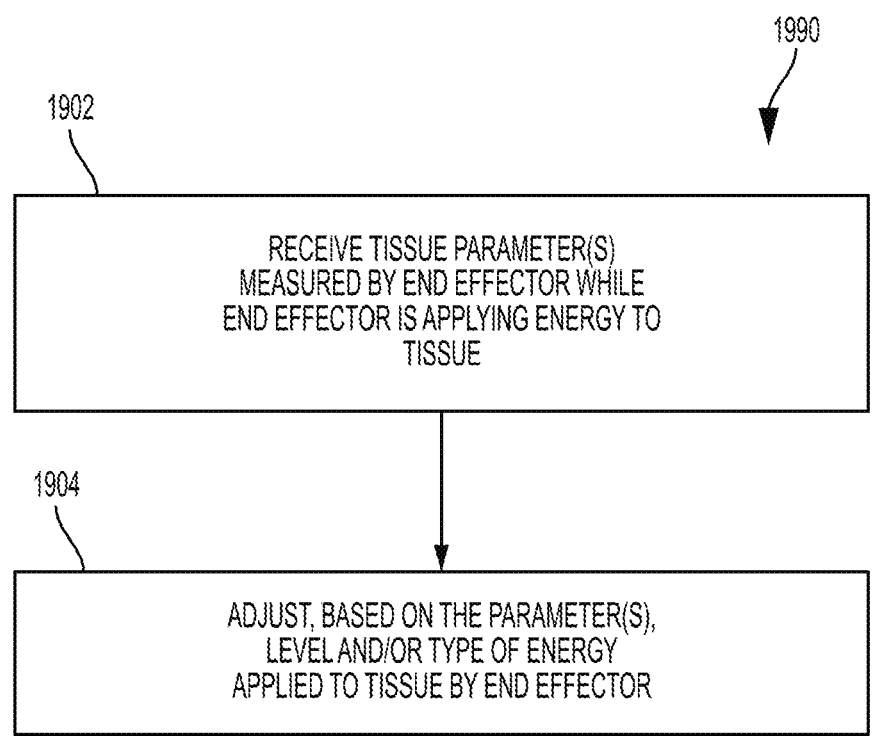
FIG. 19 illustrates an embodiment of a process for controlling an application of energy to tissue.

FIG. 19 illustrates an embodiment of a process 1900 for controlling an application of energy to tissue. The process 1900 can be performed by a robotic surgical system (e.g., the robotic surgical system 300 in FIG. 1) to automate a lift of an electromechanical tool (e.g., tool 330 or 430) having an end effector (e.g., end effector 438 or 1400) adapted to apply ultrasonic energy to tissue coupled thereto. The electromechanical tool can be coupled to a robotic arm (e.g., arm 320 or 420) and can be controlled to be lifted together with the arm, as the arm is being lifted. Additionally or alternatively, the electromechanical tool can be configured to be lifted independently of the robotic arm.

The process 1900 can start when the end effector is activated to treat tissue by at least applying one or more forms of energy thereto. A person skilled in the art will understand that the process of cutting and cauterizing tissue is performed as part of a surgical procedure that includes other steps (e.g., preparation of the tissue and surgical site, setting and activation of the surgical system, etc.) that are not described herein.

The surgical robotic system can receive one or more tissue parameters measured by an end effector while the end effector is applying at least one type of energy to the tissue (1902). For example, an end effector can be configured to apply RF energy, ultrasonic energy, and/or a combination of both. Moreover, the end effector can include one or more sensors (e.g., strain gauge, temperature sensor) configured to measure one or more parameters including, for example, temperature and tension at the tissue. In some embodiments, the end effector can be configured to measure the one or more parameters while applying RF and/or ultrasonic energy to the tissue and provide these measurements to the surgical robotic system.

The surgical robotic system can adjust, based on the one or more parameters, a level and/or type of energy applied to the tissue by the end effector (1904). In some embodiments, based on the temperature and/or tension at the tissue, the surgical robotic system can increase (or decrease) the power applied to the tissue. Moreover, based on the temperature and/or tension at the tissue, the surgical robotic system can also change the forms of energy applied to the tissue. For example, the surgical robotic system can increase the power applied to the tissue when the tension at the tissue is high due to tissue characteristics including, for example, the roughness, stiffness, and/or thickness of the tissue. The surgical robotic system can also increase the power applied to the tissue when the tension at the tissue is high due to a fast moving end effector. In instances where the tissue tension is too high (e.g., exceeds the force limit F shown in FIG. 18B), the surgical robotic system can introduce an additional type of energy (e.g., apply a combination of RF and ultrasonic energy) to treat the tissue.

It should be appreciated that the process 1900 can include additional and/or different operations than shown without departing from the scope of the present disclosure. Moreover, one or more operations of the process 1900 can be omitted and/or repeated without departing from the scope of the present disclosure.

Reuse

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345, entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
    an electromechanical arm configured for movement in multiple axes;
    an electromechanical tool having an instrument shaft and an end effector formed thereon, the electromechanical tool being configured to be mounted on the electromechanical arm, and the electromechanical tool being configured to move with or relative to the electromechanical arm and apply energy to tissue engaged by the end effector; and
    a controller operatively coupled to the electromechanical arm and the electromechanical tool, the controller configured to:
        receive, during an application of radio frequency (RF) energy to the tissue, a plurality of measurements of a plurality of parameters, the received plurality of measurements including a measure of force exerted by the tissue against the end effector; and
        adjust, based on the received plurality of measurements, a level and a type of energy applied to the tissue by the end effector, wherein the adjustment includes additionally applying ultrasonic energy in response to the measured force exceeding a predetermined force limit.

2. The surgical system of claim 1, wherein the plurality of parameters include temperature at the tissue.

3. The surgical system of claim 2, wherein the controller is configured to adjust the power by increasing the power when the temperature of the tissue is below a first threshold value and decreasing the power when the temperature of the tissue is above a second threshold value.

4. The surgical system of claim 1, wherein the end effector includes a strain gauge adapted to measure the force by measuring a load on the end effector.

5. The surgical system of claim 1, wherein the force exerted by the tissue on the end effector corresponds to a velocity of a movement of the end effector through and/or along the tissue.

6. The surgical system of claim 1, wherein the controller is configured to adjust the rate of power by decreasing the power when the force exerted by the tissue on the end effector is below a first threshold value and increasing the power when the force exerted by the tissue on the end effector is above a second threshold value.

7. The surgical system of claim 6, wherein the power remains substantially constant when the force exerted by the tissue on the end effector is equal to or above the first threshold value and is equal to or below the second threshold value.

8. The surgical system of claim 1, wherein the controller is configured to adjust the type of energy by causing the end effector to apply an additional type of energy when the force exerted by the tissue on the end effector exceeds a threshold value.

9. The surgical system of claim 1, wherein the controller is configured to adjust the type of energy by causing the end effector to switch between application of ultrasound and RF energy based on the measuring the force exerted by the tissue on the end effector.

10. The surgical system of claim 1, wherein the electromechanical tool is configured to apply energy to the tissue when the tissue is held by the end effector.

11. A method of operating a surgical instrument, comprising:
    applying at least one type of energy to a tissue using a surgical instrument formed on an instrument shaft of an electromechanical tool, the electromechanical tool being configured to be mounted on an electromechanical arm;

receiving, during an application of radio frequency (RF) energy to the tissue, a plurality of measurements of at least one parameter, the received plurality of measurements including a measure of force exerted by the tissue against the end effector; and adjusting, based on the plurality of measurements, a level and a type of energy applied to the tissue by the end effector, wherein the adjustment includes additionally applying ultrasonic energy in response to the measured force exceeding a predetermined force limit.

12. The method of claim 11, wherein at least one parameter includes a temperature of the tissue.

13. The method of claim 12, wherein the adjusting of the rate of power includes increasing the power when the temperature of the tissue is below a first threshold value and decreasing the power when the temperature of the tissue is above a second threshold value.

14. The method of claim 13, wherein the adjusting of the power includes decreasing the power when the tension at the tissue is below a first threshold value and increasing the power when the tension at the tissue is above a second threshold value.

15. The method of claim 11, wherein the at least one parameter includes a tension at the tissue.

16. The method of claim 15, wherein the adjusting of the type of energy includes causing the end effector to apply an additional type of energy when the tension at the tissue exceeds a threshold.

17. The method of claim 11, wherein the tension at the tissue corresponds to a velocity of a movement of the end effector through the tissue.

* * * * *